United States Patent
Ito et al.

(10) Patent No.: US 8,288,490 B2
(45) Date of Patent: *Oct. 16, 2012

(54) PROCESS FOR PRODUCING CATALYST COMPONENT FOR ADDITION POLYMERIZATION

(75) Inventors: Kazuyuki Ito, Ichihara (JP); Kazuo Takaoki, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/176,820

(22) Filed: Jul. 6, 2011

(65) Prior Publication Data
US 2012/0053306 A1 Mar. 1, 2012

(30) Foreign Application Priority Data

Aug. 31, 2010 (JP) ................. 2010-193378

(51) Int. Cl.
*C08F 4/44* (2006.01)
*B01J 31/00* (2006.01)
*C07F 3/00* (2006.01)

(52) U.S. Cl. ........ 526/151; 526/122; 502/104; 556/130; 556/119

(58) Field of Classification Search .................. 526/151, 526/122; 502/104; 556/130, 119
See application file for complete search history.

(56) References Cited

U.S. PATENT DOCUMENTS

| 5,113,477 A * | 5/1992 | Eguchi et al. ................. 385/143 |
| 2001/0020075 A1 | 9/2001 | Takaoki et al. |
| 2004/0209767 A1 * | 10/2004 | Takaoki ........................ 502/152 |

OTHER PUBLICATIONS

Wang et al, "A novel catalyst zinc(II) perfluoroctanoate [Zn(PFO)2]-catalyzed three-component one-pot reaction: Synthesis of quinazolinonederivatives in aqueous micellar media," Journal of Fluorine Chemistry, vol. 129, pp. 1139-1145 (2008).
Ardon et al, "Cryoscopy in Acidic and Basic Aqueous Solvents. II. Eutetic Trifluoroacetic Acid," Inorganic Chemistry, vol. 15, No. 1, pp. 12-14 (1976).

* cited by examiner

*Primary Examiner* — William Cheung
(74) *Attorney, Agent, or Firm* — Panitch Schwarze Belisario & Nadel LLP

(57) ABSTRACT

A production process of a contact product, which can be used as a polymerization catalyst component, comprising contacting a metal oxide such as zinc oxide with a compound defined by a specific formula such as trifluoroacetic acid; a production process of a polymerization catalyst, comprising contacting the polymerization catalyst component with a transition metal compound; and a production process of a polymer, comprising polymerizing an addition-polymerizable monomer in the presence of the polymerization catalyst.

12 Claims, No Drawings

PROCESS FOR PRODUCING CATALYST COMPONENT FOR ADDITION POLYMERIZATION

FIELD OF THE INVENTION

The present invention relates to a process for producing a contact product useful as a catalyst component for addition polymerization; a process for producing an addition polymerization catalyst using the contact product; and a process for producing an addition polymer using the addition polymerization catalyst.

BACKGROUND OF THE INVENTION

For example, JP 2001-181327A (corresponding to US 2001/0020075A) discloses an ethylene-hexene copolymer having weight average molecular weight (Mw) of 97,000, which is produced using an olefin polymerization catalyst formed by contacting with one another bis(pentafluorophenoxy)zinc, ethylenebis(indenyl)zirconium chloride, and triisobutylaluminum.

SUMMARY OF THE INVENTION

However, the above ethylene-hexene copolymer does not have satisfactorily high molecular weight.

In view of the above circumstances, an object of the present invention is to provide (i) a process for producing a contact product, (ii) a process for producing an addition polymerization catalyst using the contact product as a catalyst component for addition polymerization, and (iii) a process for producing a satisfactorily high molecular weight addition polymer using the addition polymerization catalyst.

The present invention is a process for producing a contact product, comprising contacting a metal oxide with a compound represented by following formula [1] or [2]:

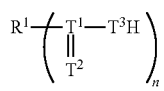   [1]

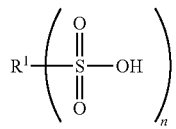   [2]

wherein $R^1$ is a monovalent, divalent, trivalent or tetravalent halogenated hydrocarbyl group having 1 to 20 carbon atoms; $T^1$ is a carbon atom or a sulfur atom; $T^2$ is an oxygen atom or a sulfur atom; $T^3$ is a group 16 atom of the periodic table; and n is an integer of 1 to 4.

Also, the present invention is a process for producing an addition polymerization catalyst, comprising contacting with one another a contact product produced by the above process, which is used as a catalyst component for addition polymerization, a transition metal compound of groups 3 to 11 of the periodic table, and an optional organoaluminum compound.

The above process for producing an addition polymerization catalyst using the contact product and the transition metal compound of groups 3 to 11 is referred to hereinafter as "polymerization catalyst production process-1", and the above process for producing an addition polymerization catalyst using the contact product, the transition metal compound of groups 3 to 11, and the organoaluminum compound is referred to hereinafter as "polymerization catalyst production process-2". Each of the above transition metal compound and organoaluminum compound is also a kind of catalyst component, because they are used for making a polymerization catalyst.

Further, the present invention is a process for producing an addition polymer, comprising polymerizing an addition-polymerizable monomer in the presence of an addition polymerization catalyst produced by the above process.

DETAILED DESCRIPTION OF THE INVENTION

Examples of the above metal oxide are a metal oxide of a typical element selected from groups 1, 2 and 12 to 18 of the periodic table, such as beryllium oxide, magnesium oxide, aluminum oxide, calcium oxide, zinc oxide, potassium oxide, germanium oxide, cadmium oxide, and mercury oxide; and a metal oxide of a transition element selected from groups 3 to 11 of the periodic table such as strontium oxide, scandium oxide, titanium oxide, vanadium oxide, chromium oxide, manganese oxide, yttrium oxide, zirconium oxide, niobium oxide, and molybdenum oxide.

The metal oxide is preferably a metal oxide of a typical element selected form groups 1, 2 and 12 to 18 of the periodic table; more preferably a metal oxide of a typical element of group 12 of the periodic table such as zinc oxide, cadmium oxide and mercury oxide, manganese oxide, aluminum oxide or calcium oxide; further preferably a metal oxide of a typical element of group 12 of the periodic table such as zinc oxide, cadmium oxide and mercury oxide; and most preferably zinc oxide.

Examples of above $R^1$ are a perfluoromethyl group, a 1,2,2,2-tetrafluoroethyl group, a perfluoroethyl group, a perfluoro(n-propyl) group, a 2,2,2-trifluoro-1-trifluoromethylethyl group, a perfluoroisopropyl group, a perfluoro(n-butyl) group, a perfluoro(sec-butyl) group, a perfluoroisobutyl group, a perfluoro(tert-butyl) group, a perfluoro(n-pentyl) group, a perfluoro(n-hexyl) group, a perfluorocyclohexyl group, a pentafluorophenyl group, a perfluoro(n-heptyl) group, a perfluoro(n-octyl) group, a perfluoro(n-nonyl) group, a perfluoro(n-decyl) group, a perfluorodecahydronaphthyl group, a perfluoro(n-undecyl) group, a perfluoro(n-dodecyl) group, a perfluoro(n-tridecyl) group, a perfluoro(n-pentadecyl) group, a perfluoro(n-heptadecyl) group, a perfluoromethylene group, a trifluoroethylene group, a perfluoroethylene group, a perfluoropropylene group, a perfluorobutylene group, a perfluoropentylene group, a perfluorohexylene group, a perfluoroheptylene group, a perfluorooctylene group, and a perfluorodecylene group; and groups obtained by changing "fluoro" contained in the above groups to "chloro", "bromo" or "iodo".

$R^1$ is preferably a monovalent or divalent fluorinated hydrocarbyl group having 1 to 20 carbon atoms. The fluorinated hydrocarbyl group having 1 to 20 carbon atoms is (1) preferably a linear, branched or cyclic fluorinated hydrocarbyl group having 1 to 10 carbon atoms, (2) more preferably a monovalent linear, branched or cyclic fluorinated hydrocarbyl group having 2 to 10 carbon atoms such as a 1,2,2,2-tetrafluoroethyl group, a perfluoroethyl group, a perfluoro(n-propyl) group, a 2,2,2-trifluoro-1-trifluoromethylethyl group, a perfluoroisopropyl group, a perfluoro(n-butyl) group, a perfluoro(sec-butyl) group, a perfluoroisobutyl group, a perfluoro(tert-butyl) group, a perfluoro(n-pentyl) group, a perfluoro(n-hexyl) group, a perfluorocyclohexyl group, a pentafluorophenyl group, a perfluoro(n-heptyl) group, a perfluoro(n-octyl) group, a perfluoro(n-nonyl) group, a perfluoro (n-decyl) group, and a perfluorodecahydronaphthyl group; or a divalent linear, branched or cyclic perfluorocarbyl group having 1 to 10 carbon atoms such as a perfluoromethylene group, a trifluoroethylene group, a perfluoroethylene group, a perfluoropropylene group, a perfluorobutylene group, a perfluoropentylene group, a perfluorohexylene group, a perfluoroheptylene group, a perfluorooctylene group, and a perfluorodecylene group, (3) further preferably a monovalent linear or branched fluorinated hydrocarbyl group having 2 to 10 carbon atoms such as a 1,2,2,2-tetrafluoroethyl group, a perfluoroethyl group, a perfluoro(n-propyl) group, a 2,2,2-trifluoro-1-trifluoromethylethyl group, a perfluoroisopropyl group, a perfluoro(n-butyl) group, a perfluoro(sec-butyl) group, a perfluoroisobutyl group, a perfluoro(tert-butyl) group, a perfluoro(n-pentyl) group, a perfluoro(n-hexyl) group, a perfluoro(n-heptyl) group, a perfluoro(n-octyl) group, a perfluoro(n-nonyl) group, and a perfluoro(n-decyl) group; or a divalent linear or branched perfluorocarbyl group having 1 to 10 carbon atoms such as a perfluoromethylene group, a perfluoroethylene group, a perfluoropropylene group, a perfluorobutylene group, a perfluoropentylene group, a perfluorohexylene group, a perfluoroheptylene group, a perfluorooctylene group, and a perfluorodecylene group, and (4) most preferably a perfluoroethyl group, a 2,2,2-trifluoro-1-trifluoromethylethyl group, a perfluoroisopropyl group, a perfluoro(n-pentyl) group, a perfluoromethylene group, a perfluoroethylene group, a perfluorobutylene group, a perfluoropentylene group, a perfluorohexylene group, or a perfluorooctylene group.

In above formula [1], $T^1$ is a carbon atom or a sulfur atom, and preferably a carbon atom, and $T^2$ is an oxygen atom or a sulfur atom, and preferably an oxygen atom. Examples of $T^3$ are an oxygen atom and a sulfur atom. Among them, preferred is an oxygen atom or a sulfur atom, and particularly preferred is an oxygen atom.

The compound represented by formula [1] may be a compound known in the art. Examples thereof are trifluoroacetic acid, 2,3,3,3-tetrafluoropropionic acid, pentafluoropropionic acid, heptafluorobutyric acid, 3,3,3-trifluoro-2-trifluoromethylpropionic acid, 2,3,3,3-tetrafluoro-2-trifluoromethylpropionic acid, nonafluorovaleric acid, 2,3,3,4,4,4-hexafluoro-2-trifluoromethylbutyric acid, 2,2,3,3,4,4,4-heptafluoro-3-trifluoromethylbutyric acid, 3,3,3-trifluoro-2,2-bis(trifluoromethyl)propionic acid, undecafluorohexanoic acid, tridecafluoroheptanoic acid, 1,2,2,3,3,4,4,5,5,6,6-undecafluorocyclohexane carboxylic acid, pentafluorobenzoic acid, pentadecafluorooctanoic acid, heptadecafluorononanoic acid, nonadecafluorodecanoi acid, heneicosafluoroundecanoic acid, 1,2,2,3,3,4,4,4a,5,5,6,6,7,7,8,8,8a-heptadecafluorodeca hydro-1-naphthalene carboxylic acid, tricosafluorododecanoic acid, pentacosafluorotridecanoic acid, heptacosafluorotetradecanoic acid, hentriacontafluorohexadecanoic acid, pentatriacontaoctadecanoic acid, difluoromalonic acid, trifluorosuccinic acid, tetrafluorosuccinic acid, hexafluoroglutaric acid, octafluoroadipic acid, decafluoropimelic acid, dodecafluorosuberic acid, tetradecafluoroazelaic acid, hexadecafluorosebacic acid, and eicosafluorododecanedioic acid, and a combination of two or more thereof.

Among them, preferred is trifluoroacetic acid, 2,3,3,3-tetrafluoropropionic acid, pentafluoropropionic acid, heptafluorobutyric acid, 3,3,3-trifluoro-2-trifluoromethylpropionic acid, 2,3,3,3-tetrafluoro-2-trifluoromethylpropionic acid, nonafluorovaleric acid, 2,3,3,4,4,4-hexafluoro-2-trifluoromethylbutyric acid, 2,2,3,3,4,4,4-heptafluoro-3-trifluoromethylbutyric acid, 3,3,3-trifluoro-2,2-bis(trifluoromethyl)propionic acid, undecafluorohexanoic acid, tridecafluoroheptanoic acid, 1,2,2,3,3,4,4,5,5,6,6-undecafluorocyclohexane carboxylic acid, pentafluorobenzoic acid, pentadecafluorooctanoic acid, heptadecafluorononanoic acid, nonadecafluorodecanoic acid, heneicosafluoroundecanoic acid, 1,2,2,3,3,4,4,4a,5,5,6,6,7,7,8,8,8a-heptadecafluoro decahydro-1-naphthalene carboxylic acid, difluoromalonic acid, trifluorosuccinic acid, tetrafluorosuccinic acid, hexafluoroglutaric acid, octafluoroadipic acid, decafluoropimelic acid, dodecafluorosuberic acid, tetradecafluoroazelaic acid, hexadecafluorosebacic acid, or eicosafluorododecanedioic acid; more preferred is 2,3,3,3-tetrafluoropropionic acid, pentafluoropropionic acid, heptafluorobutyric acid, 3,3,3-trifluoro-2-trifluoromethylpropionic acid, 2,3,3,3-tetrafluoro-2-trifluoromethylpropionic acid, nonafluorovaleric acid, 2,3,3,4,4,4-hexafluoro-2-trifluoromethylbutyric acid, 2,2,3,3,4,4,4-heptafluoro-3-trifluoromethylbutyric acid, 3,3,3-trifluoro-2,2-bis(trifluoromethyl)propionic acid, undecafluorohexanoic acid, tridecafluoroheptanoic acid, 1,2,2,3,3,4,4,5,5,6,6-undecafluorocyclohexane carboxylic acid, pentafluorobenzoic acid, pentadecafluorooctanoic acid, heptadecafluorononanoic acid, nonadecafluorodecanoic acid, heneicosafluoroundecanoic acid, 1,2,2,3,3,4,4,4a,5,5,6,6,7,7,8,8,8a-heptadecafluoro decahydro-1-naphthalene carboxylic acid, difluoromalonic acid, trifluorosuccinic acid, tetrafluorosuccinic acid, hexafluoroglutaric acid, octafluoroadipic acid, decafluoropimelic acid, dodecafluorosuberic acid, tetradecafluoroazelaic acid, hexadecafluorosebacic acid, or eicosafluorododecanedioic acid; further preferred is 2,3,3,3-tetrafluoropropionic acid, pentafluoropropionic acid, heptafluorobutyric acid, 3,3,3-trifluoro-2-trifluoromethylpropionic acid, 2,3,3,3-tetrafluoro-2-trifluoromethylpropionic acid, nonafluorovaleric acid, 2,3,3,4,4,4-hexafluoro-2-trifluoromethylbutyric acid, 2,2,3,3,4,4,4-heptafluoro-3-trifluoromethylbutyric acid, 3,3,3-trifluoro-2,2-bis(trifluoromethyl)propionic acid, undecafluorohexanoic acid, tridecafluoroheptanoic acid, pentadecafluorooctanoic acid, heptadecafluorononanoic acid, nonadecafluorodecanoic acid, heneicosafluoroundecanoic acid, difluoromalonic acid, tetrafluorosuccinic acid, hexafluoroglutaric acid, octafluoroadipic acid, decafluoropimelic acid, dodecafluorosuberic acid, tetradecafluoroazelaic acid, hexadecafluorosebacic acid, or eicosafluorododecanedioic acid; and most preferred is pentafluoropropionic acid, heptafluorobutyric acid, 3,3,3-trifluoro-2-trifluoromethylpropionic acid, 2,3,3,3-tetrafluoro-2-trifluoromethylpropionic acid, undecafluorohexanoic acid, difluoromalonic acid, tetrafluorosuccinic acid, octafluoroadipic acid, decafluoropimelic acid, dodecafluorosuberic acid, or hexadecafluorosebacic acid.

The compound represented by formula [2] may be a compound known in the art. Examples thereof are trifluoromethanesulfonic acid, 2,3,3,3-tetrafluoroethanesulfonic acid, pentafluoroethanesulfonic acid, 3,3,3-trifluoro-2-trifluoromethylethanesulfonic acid, 2,3,3,3-tetrafluoro-2-trifluoromethylethanesulfonic acid, 1-heptafluoropropanesulfonic acid, 2,2,2-trifluoro-1-trifluoromethylethanesulfonic acid, 1,2,2,2-tetrafluoro-1-trifluoromethylethanesulfonic acid, 1-nonafluorobutanesulfonic acid, 1,2,2,3,3,3-hexafluoro-1-trifluoromethylpropanesulfonic acid, 1,1,2,2,3,3,3-heptafluoro-2-trifluoromethylpropanesulfonic acid, 2,2,2-trifluoro-1,1-bis(trifluoromethyl)ethanesulfonic acid, 1-undecafluoropentanesulfonic acid, 1-tridecafluorohexanesulfonic acid, 1,2,2,3,3,4,4,5,5,6,6-undecafluorocyclohexanesulfonic acid, pentafluorobenzenesulfonic acid, pentadecafluoroheptanesulfonic acid, heptadecafluorooctanesulfonic acid, nonadecafluorononanesulfonic acid, heneicosafluorodecanesulfonic acid, 1,2,2,3,3,4,4,4a,5,5,6,6,7,7,8,8,8a-heptadecafluoro decahydro-1-naphthalenesulfonic acid, tricosafluoroundecanesulfonic acid, pentacosafluorododecanesulfonic acid, heptacosafluorotridecanesulfonic acid, hentriacontafluoropentadecanesulfonic acid, pentatriacontafluoroheptadecanesulfonic acid, difluoromethanedisulfonic acid, trifluoroethanedisulfonic acid, tetrafluoroethanedisulfonic acid, hexafluoropropanedisulfonic acid, octafluorobutanedisulfonic acid, decafluoropentanedisulfonic acid, dodecafluorohexanedisulfonic acid, tetradecafluoroheptanedisulfonic acid, hexadecafluorooctanedisulfonic acid, and eicosafluorodecanedisulfonic acid, and a combination of two or more of the above compounds.

Among them, preferred is trifluoromethanesulfonic acid, 2,3,3,3-tetrafluoroethanesulfonic acid, pentafluoroethanesulfonic acid, 3,3,3-trifluoro-2-trifluoromethylethanesulfonic acid, 2,3,3,3-tetrafluoro-2-trifluoromethylethanesulfonic acid, 1-heptafluoropropanesulfonic acid, 2,2,2-trifluoro-1-trifluoromethylethanesulfonic acid, 1,2,2,2-tetrafluoro-1-trifluoromethylethanesulfonic acid, 1-nonafluorobutanesulfonic acid, 1,2,2,3,3,3-hexafluoro-1-trifluoromethylpropanesulfonic acid, 1,1,2,2,3,3,3-heptafluoro-2-trifluoromethylpropanesulfonic acid, 2,2,2-trifluoro-1,1-bis(trifluoromethyl)ethanesulfonic acid, 1-undecafluoropentanesulfonic acid, 1-tridecafluorohexanesulfonic acid, 1,2,2,3,3,4,4,5,5,6,6-undecafluorocyclohexanesulfonic acid, pentafluorobenzenesulfonic acid, pentadecafluoroheptanesulfonic acid, heptadecafluorooctanesulfonic acid, nonadecafluorononanesulfonic acid, heneicosafluorodecanesulfonic acid, 1,2,2,3,3,4,4,4a,5,5,6,6,7,7,8,8,8a-heptadecafluoro decahydro-1-naphthalenesulfonic acid, difluoromethanedisulfonic acid, trifluoroethanedisulfonic acid, tetrafluoroethanedisulfonic acid, hexafluoropropanedisulfonic acid, octafluorobutanedisulfonic acid, decafluoropentanedisulfonic acid, dodecafluorohexanedisulfonic acid, tetradecafluoroheptanedisulfonic acid, hexadecafluorooctanedisulfonic acid, or eicosafluorodecanedisulfonic acid; more preferred is 2,3,3,3-tetrafluoroethanesulfonic acid, pentafluoroethanesulfonic acid, 3,3,3-trifluoro-2-trifluoromethylethanesulfonic acid, 2,3,3,3-tetrafluoro-2-trifluoromethylethanesulfonic acid, 1-heptafluoropropanesulfonic acid, 2,2,2-trifluoro-1-trifluoromethylethanesulfonic acid, 1,2,2,2-tetrafluoro-1-trifluoromethylethanesulfonic acid, 1-nonafluorobutanesulfonic acid, 1,2,2,3,3,3-hexafluoro-1-trifluoromethylpropanesulfonic acid, 1,1,2,2,3,3,3-heptafluoro-2-trifluoromethylpropanesulfonic acid, 2,2,2-trifluoro-1,1-bis(trifluoromethyl)ethanesulfonic acid, 1-undecafluoropentanesulfonic acid, 1-tridecafluorohexanesulfonic acid, 1,2,2,3,3,4,4,5,5,6,6-undecafluorocyclohexanesulfonic acid, pentafluorobenzenesulfonic acid, pentadecafluoroheptanesulfonic acid, heptadecafluorooctanesulfonic acid, nonadecafluorononanesulfonic acid, heneicosafluorodecanesulfonic acid, 1,2,2,3,3,4,4,4a,5,5,6,6,7,7,8,8,8a-heptadecafluoro decahydro-1-naphthalenesulfonic acid, difluoromethanedisulfonic acid, trifluoroethanedisulfonic acid, tetrafluoroethanedisulfonic acid, hexafluoropropanedisulfonic acid, octafluorobutanedisulfonic acid, decafluoropentanedisulfonic acid, dodecafluorohexanedisulfonic acid, tetradecafluoroheptanedisulfonic acid, hexadecafluorooctanedisulfonic acid, or eicosafluorodecanedisulfonic acid; further preferred is 2,3,3,3-tetrafluoroethanesulfonic acid, pentafluoroethanesulfonic acid, 3,3,3-trifluoro-2-trifluoromethylethanesulfonic acid, 2,3,3,3-tetrafluoro-2-trifluoromethylethanesulfonic acid, 1-heptafluoropropanesulfonic acid, 2,2,2-trifluoro-1-trifluoromethylethanesulfonic acid, 1,2,2,2-tetrafluoro-1-trifluoromethylethanesulfonic acid, 1-nonafluorobutanesulfonic acid, 1,2,2,3,3,3-hexafluoro-1-trifluoromethylpropanesulfonic acid, 1,1,2,2,3,3,3-heptafluoro-2-trifluoromethylpropanesulfonic acid, 2,2,2-trifluoro-1,1-bis(trifluoromethyl)ethanesulfonic acid, 1-undecafluoropentanesulfonic acid, 1-tridecafluorohexanesulfonic acid, pentadecafluoroheptanesulfonic acid, heptadecafluorooctanesulfonic acid, nonadecafluorononanesulfonic acid, heneicosafluorodecanesulfonic acid, difluoromethanedisulfonic acid, trifluoroethanedisulfonic acid, tetrafluoroethanedisulfonic acid, hexafluoropropanedisulfonic acid, octafluorobutanedisulfonic acid, decafluoropentanedisulfonic acid, dodecafluorohexanedisulfonic acid, tetradecafluoroheptanedisulfonic acid, hexadecafluorooctanedisulfonic acid, or eicosafluorodecanedisulfonic acid; and most preferred is pentafluoroethanesulfonic acid, 3,3,3-trifluoro-2-trifluoromethylethanesulfonic acid, 2,3,3,3-tetrafluoro-2-trifluoromethylethanesulfonic acid, 1-undecafluoropentanesulfonic acid, difluoromethanedisulfonic acid, tetrafluoroethanedisulfonic acid, octafluorobutanedisulfonic acid, decafluoropentanedisulfonic acid, dodecafluorohexanedisulfonic acid, or hexadecafluorooctanedisulfonic acid.

The contact of the metal oxide with the compound represented by formula [1] or [2] is carried out under an inert gas atmosphere or air atmosphere, at usually −100 to 300° C., preferably −80 to 200° C., more preferably 0 to 100° C., and further preferably 0 to 40° C., for usually 1 minute to 200 hours, preferably 10 minutes to 100 hours, and more preferably 10 minutes to 20 hours, in the presence or absence of a solvent.

The solvent is inactive against the metal oxide, the compound represented by formula [1] or [2], and a contact product of them. Examples of the solvent are a nonpolar solvent such as an aliphatic hydrocarbyl solvent, an alicyclic hydrocarbyl solvent, and an aromatic hydrocarbyl solvent; and a polar solvent such as water, a halogen atom-containing solvent, an ether solvent, a carbonyl group-containing solvent, a phosphoric acid derivative, a nitrile solvent, a nitro compound, an amine solvent, and a sulfur compound. Among them, preferred is an aliphatic hydrocarbyl solvent, an alicyclic hydrocarbyl solvent, an aromatic hydrocarbyl solvent, an ether solvent, or water, and more preferred is an ether solvent or water.

Examples of the above aliphatic hydrocarbyl solvent are butane, pentane, hexane, heptane, octane, and 2,2,4-trimethylpentane. An example of the above alicyclic hydrocarbyl solvent is cyclohexane. Examples of the above aromatic hydrocarbyl solvent are benzene, toluene and xylene.

Examples of the above halogen atom-containing solvent are dichloromethane, difluoromethane, chloroform, 1,2-dichloroethane, 1,2-dibromoethane, 1,1,2-trichloro-1,2,2-trifluoroethane, tetrachloroethylene, chlorobenzene, bromobenzene, and o-dichlorobenzene. Examples of the above ether solvent are dimethyl ether, diethyl ether, diisopropyl ether, di-n-butyl ether, methyl tert-butyl ether, anisole, 1,4-dioxane, 1,2-dimethoxyethane, bis(2-methoxyethyl)ether, tetrahydrofuran, and tetrahydropyran. Examples of the above carbonyl group-containing solvent are acetone, ethyl methyl ketone, cyclohexanone, acetic anhydride, ethyl acetate, butyl acetate, ethylene carbonate, propylene carbonate, N,N-dimethylformamide, N,N-dimethylacetamide, and N-methyl-2-pyrrolidone, Examples of the above phosphoric acid derivative are hexamethylphosphoric triamide and triethyl phosphate. Examples of the above nitrile solvent are acetonitrile, propionitrile, succinonitrile, and benzonitrile. Examples of the above nitro compound are nitromethane and nitrobenzene. Examples of the above amine solvent are pyridine, piperidine and morpholine. Examples of the above sulfur compound are dimethylsulfoxide and sulfolane.

The compound represented by formula [1] or [2] is used in a lower limit amount of more than 0 (zero) mol, preferably 0.3 mol or more, more preferably 0.5 mol or more, and most preferably 1 mol or more, and in an upper limit amount of preferably 100 mol or less, more preferably 10 mol or less, and most preferably 4 mol or less, which are a molar amount of an active hydrogen contained in the compound represented by formula [1] or [2] used, per one mol of a metal atom contained in the metal oxide used.

A contact product obtained by contacting the metal oxide with the compound represented by formula [1] or [2] may contain the unreacted metal oxide and/or compound. In order to remove the unreacted metal oxide and/or compound, the contact product is preferably washed under an inert gas atmosphere or air atmosphere with a solvent, which is the same as, or different from the above solvent used for the contact of the metal oxide with the compound represented by formula [1] or [2], at usually −100 to 300° C., preferably −80 to 200° C., more preferably 0 to 100° C., and further preferably 0 to 40° C., for usually 1 minute to 200 hours, and preferably 10 minutes to 100 hours. The washed contact product is vacuum dried preferably at 0° C. or higher for 1 to 24 hours, more preferably at 0 to 200° C. for 1 to 24 hours, further preferably at 10 to 200° C. for 1 to 24 hours, particularly preferably at 10 to 160° C. for 1 to 18 hours, and most preferably at 15 to 160° C. for 1 to 18 hours.

The following is a specific explanation of the production process of the present invention, provided that the metal oxide, the compound represented by formula [1], and the compound represented by formula [2] are zinc oxide, a halogenated hydrocarbyl group-containing carboxylic acid, and a halogenated hydrocarbyl group-containing sulfonic acid, respectively:

(1) zinc oxide is added to water (solvent);
(2) to the resultant aqueous mixture is added by drops the halogenated hydrocarbyl group-containing carboxylic acid, or the halogenated hydrocarbyl group-containing sulfonic acid in an amount of more than 0 (zero) to 4 mol of an active hydrogen contained in those acids used, per one mol of a zinc atom contained in zinc oxide used;
(3) the obtained mixture is stirred at 0 to 100° C. for 10 minutes to 24 hours, thereby obtaining a reaction mixture;
(4) insoluble materials contained in the reaction mixture are filtered off;
(5) volatile materials contained in the obtained filtrate are vacuum-distilled away; and
(6) the resultant solid is vacuum-dried at room temperature for 1 to 20 hours, thereby obtaining a contact product.

The above contact product can be used as a catalyst component for producing an addition polymerization catalyst. Therefore, the above process for producing a contact product is also a process for producing a catalyst component for addition polymerization, comprising contacting a metal oxide with a compound represented by above formula [1] or [2]. The catalyst component may be supported on a carrier. The carrier is preferably a porous material having a uniform particle diameter, and is preferably an inorganic material or an organic polymer. Examples of the inorganic material are an inorganic oxide (including the above metal oxide), a magnesium compound, clay, a clay mineral, and a combination of two or more thereof.

Examples of the above inorganic oxide are $SiO_2$, $Al_2O_3$, $MgO$, $ZrO_2$, $TiO_2$, $B_2O_3$, $CaO$, $ZnO$, $BaO$ and $ThO_2$, and a mixture of two or more thereof such as $SiO_2$—$MgO$, $SiO_2$—$Al_2O_3$, $SiO_2$—$TiO_2$, $SiO_2$—$V_2O_5$, $SiO_2$—$Cr_2O_3$ and $SiO_2$—$TiO_2$—$MgO$. Among them, preferred is $SiO_2$ and/or $Al_2O_3$. Those inorganic oxides may contain a small amount of carbonates, sulfates, nitrates or oxides such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$.

Examples of the above magnesium compound are a magnesium halide such as magnesium chloride, magnesium bromide, magnesium iodide, and magnesium fluoride; an alkoxymagnesium halide such as methoxymagnesium chloride, ethoxymagnesium chloride, isopropoxymagnesium chloride, butoxymagnesium chloride, and octoxymagnesium chloride; an aryloxymagnesium halide such as phenoxymagnesium chloride and methylphenoxymagnesium chloride; an alkoxymagnesium such as ethoxymagnesium, isopropoxymagnesium, butoxymagnesium, n-octoxymagnesium, and 2-ethylhexoxymagnesium; an aryloxymagnesium such as phenoxymagnesium and dimethylphenoxymagnesium; and a magnesium carboxylate such as magnesium laurate and magnesium stearate. Among them, preferred is a magnesium halide or an alkoxymagnesium, and further preferred is magnesium chloride or butoxymagnesium.

Examples of above clay and clay mineral are kaolin, bentonite, kibushi clay, gaerome clay, allophane, hisingerite, pyrophylite, talc, a mica group, smectite, hectorite, raponite, saponite, a montmorillonite group, vermiculite, a chlorite group, palygorskite, kaolinite, nacrite, smectite, hectorite, raponite, saponite, dickite, and halloycite. Among them, preferred is smectite, montmorillonite, hectorite, raponite or saponite, and further preferred is montmorillonite or hectorite.

The above inorganic material is preferably dried. Examples of the drying method are (1) a method comprising flowing a dried inert gas (such as nitrogen and argon) at a constant flowing speed for a couple of hours or more, and (2) a method comprising exposing the inorganic material to a vacuum for a couple of hours, both methods (1) and (2) being carried out under heating the inorganic material at usually 100 to 1,500° C., preferably 100 to 1,000° C., and further preferably 200 to 800° C.

The above inorganic material has (1) a number-average particle diameter of preferably 5 to 1,000 µm, more preferably 10 to 500 µm, and further preferably 10 to 100 µm, (2) a pore volume of preferably 0.1 mL/g or more, and more preferably 0.3 to 10 mL/g, and (3) a specific surface area of preferably 10 to 1,000 $m^2/g$, and more preferably 100 to 500 $m^2/g$.

The above organic polymer has preferably a non-proton-donating Lewis basic functional group, which means a Lewis basic functional group having no ability to donate a proton, and which is not particularly limited as long as the functional group has a Lewis basic part containing no active hydrogen. Examples of the non-proton-donating Lewis basic functional group are a pyridyl group, an N-substituted imidazolyl group, an N-substituted indazolyl group, a nitrile group, an azido group, an N-substituted imino group, an N,N-disubstituted amino group, an N,N-disubstituted aminoxy group, an N,N,N-trisubstituted hydrazino group, a nitroso group, a nitro group, a nitroxy group, a furyl group, a carbonyl group, a thiocarbonyl group, an alkoxy group, an alkyloxycarbonyl group, an N,N-disubstituted carbamoyl group, a thioalkoxy group, a substituted sulfinyl group, a substituted sulfonyl group, and a substituted sulfonic acid group. Among them, preferred is a heterocyclic group; further more preferred is an aromatic heterocyclic group having an oxygen atom and/or nitrogen atom in its ring; particularly preferred is a pyridyl group, an N-substituted imidazolyl group, or an N-substituted indazoyl group; and most preferred is a pyridyl group. Those groups may be substituted with a halogen atom, or a hydrocarbyl group having 1 to 20 carbon atoms.

An amount of the above non-proton-donating Lewis basic functional group contained in the organic polymer is not particularly limited, and is preferably 0.01 to 50 mmol, and more preferably 0.1 to 20 mmol of the functional group contained therein, per one gram of the organic polymer.

The above organic polymer having a non-proton-donating Lewis basic functional group can be produced, for example, (1) by homopolymerizing a monomer having both a non-proton-donating Lewis basic functional group and one or more polymerizable unsaturated groups, or (2) by copolymerizing such a monomer with other monomer having one or more polymerizable unsaturated groups. These monomers are preferably combined with a crosslinkable monomer having two or more polymerizable unsaturated groups, such as divinylbenzene.

Examples of the above monomer having both a non-proton-donating Lewis basic functional group and one or more polymerizable unsaturated groups are those having (1) a functional group, which has the above Lewis basic part containing no active hydrogen, and (2) one or more polymerizable unsaturated groups. Examples of the polymerizable unsaturated group are an alkenyl group such as a vinyl group and an allyl group; and an alkynyl group such as an ethyne group. Specific examples of the above monomer are vinylpyridine, vinyl(N-substituted)imidazole and vinyl(N-substituted)indazole.

Examples of above other monomer having one or more polymerizable unsaturated groups are ethylene; an α-olefin such as propylene, butene-1, hexene-1 and 4-methyl-pentene-1; an aromatic vinyl compound such as styrene; and a combination of two or more thereof. Among them, preferred is ethylene or styrene.

The above organic polymer has (1) a number-average particle diameter of preferably 5 to 1,000 μm, and more preferably 10 to 500 μm, (2) a pore volume of preferably 0.1 mL/g or more, and more preferably 0.3 to 10 mL/g, and (3) a specific surface area of preferably 10 to 1,000 m$^2$/g, and more preferably 50 to 500 m$^2$/g.

Examples of a method for supporting the above catalyst component (namely, the above contact product) on a carrier are (1) a method comprising steps of (1-1) producing a catalyst component, and (1-2) supporting the catalyst component on a carrier, and (2) a method comprising producing a catalyst component in the presence of a carrier, thereby obtaining the catalyst component supported on the carrier.

Examples of the transition metal compound of groups 3 to 11 of the periodic table in the present invention are a compound represented by following formula [3], and a μ-oxo type compound thereof:

$$(L^1)_c M^1 (X^1)_{a-b \times c} \quad [3]$$

wherein $M^1$ is a transition metal atom of groups 3 to 11 of the periodic table (IUPAC, 1989); $L^1$ is a cyclopentadiene-containing anionic group having 5 to 30 carbon atoms, or a hetero atom-containing group, and when two or more $L^1$s exist, they are the same as, or different from one another, and they may be linked to one another directly or through a inking group containing a carbon atom, a silicone atom, a nitrogen atom, an oxygen atom, a sulfur atom, or a phosphorus atom; $X^1$ is a halogen atom, a hydrocarbyl group having 1 to 20 carbon atoms, or a hydrocarbyloxy group having 1 to 20 carbon atoms, and when two or more $X^1$s exist, they are the same as, or different from one another; a is a valence of $M^1$; b is a valence of $L^1$; and c is an integer satisfying a−b×c>0.

Examples of $M^1$ are a titanium atom, a zirconium atom, a hafnium atom, a vanadium atom, a niobium atom, a tantalum atom, a chromium atom, an iron atom, a ruthenium atom, a cobalt atom, a rhodium atom, a nickel atom, and a palladium atom. Among them, preferred is a transition metal atom of group 4, a nickel atom, or a palladium atom, more preferred is a titanium atom, a zirconium atom, or a hafnium atom, and further preferred is a zirconium atom.

Examples of the above cyclopentadiene-containing anionic group having 5 to 30 carbon atoms of $L^1$ are a cyclopentadienyl group, a substituted cyclopentadienyl group, an indenyl group, a substituted indenyl group, a fluorenyl group, a substituted fluorenyl group, an azulenyl group, a substituted azulenyl group, a hexahydroazulenyl group, a substituted hexahydroazulenyl group, a hydroazulenyl group, and a substituted hydroazulenyl group. Among them, preferred is a $\eta^5$-(substituted)cyclopentadienyl group, a $\eta^5$-(substituted)indenyl group, or a $\eta^5$-(substituted)fluorenyl group.

Specific examples of the cyclopentadiene-containing anionic group are an $\eta^5$-cyclopentadienyl group, an $\eta^5$-methylcyclopentadienyl group, an $\eta^5$-tert-butylcyclopentadienyl group, an $\eta^5$-1,2-dimethylcyclopentadienyl group, an $\eta^5$-1,3-dimethylcyclopentadienyl group, an $\eta^5$-1-tert-butyl-2-methylcyclopentadienyl group, an $\eta^5$-1-tert-butyl-3-methylcyclopentadienyl group, an $\eta^5$-1-methyl-2-isopropylcyclopentadienyl group, an $\eta^5$-1-methyl-3-isopropylcyclopentadienyl group, an $\eta^5$-1,2,3-trimethylcyclopentadienyl group, an $\eta^5$-1,2,4-trimethylcyclopentadienyl group, an $\eta^5$-tetramethylcyclopentadienyl group, an $\eta^5$-pentamethylcyclopentadienyl group, an $\eta^5$-indenyl group, an $\eta^5$-4,5,6,7-tetrahydroindenyl group, an $\eta^5$-2-methylindenyl group, an $\eta^5$-3-methylindenyl group, an $\eta^5$-4-methylindenyl group, an $\eta^5$-5-methylindenyl group, an $\eta^5$-6-methylindenyl group, an $\eta^5$-7-methylindenyl group, an $\eta^5$-2-tert-butylindenyl group, an $\eta^5$-3-tert-butylindenyl group, an $\eta^5$-4-tert-butylindenyl group, an $\eta^5$-5-tert-butylindenyl group, an $\eta^5$-6-tert-butylindenyl group, an $\eta^5$-7-tert-butylindenyl group, an $\eta^5$-2,3-dimethylindenyl group, an $\eta^5$-4,7-dimethylindenyl group, an $\eta^5$-2,4,7-trimethylindenyl group, an $\eta^5$-2-methyl-4-isopropylindenyl group, an $\eta^5$-4,5-benzindenyl group, an $\eta^5$-2-methyl-4,5-benzindenyl group, an $\eta^5$-4-phenylindenyl group, an $\eta^5$-2-methyl-5-phenylindenyl group, an $\eta^5$-2-methyl-4-phenylindenyl group, an $\eta^5$-2-methyl-4-naphthylindenyl group, an $\eta^5$-fluorenyl group, an $\eta^5$-2,7-dimethylfluorenyl group, an $\eta^5$-2,7-di-tert-butylfluorenyl group, an $\eta^5$-3,6-di-tert-butylfluorenyl group, an $\eta^5$-3,6-dicumylfluorenyl group, an $\eta^5$-3,6-dimethylfluorenyl group, an $\eta^5$-2,7-diphenylfluorenyl group, an $\eta^5$-3,6-diphenylfluorenyl group, an $\eta^5$-2,7-di (2,4,6-trimethylphenyl)fluorenyl group, an $\eta^5$-3,6-di(2,4,6-trimethylphenyl)fluorenyl group, an 2,7-diisopropylfluorenyl group, an $\eta^5$-3,6-diisopropylfluorenyl group, an $\eta^5$-2,7-dicyclohexylfluorenyl group, an $\eta^5$-3,6-dicyclohexylfluorenyl group, an azulenyl group, a hexahydroazulenyl group, a 2-methyl-4-phenylazulenyl group, a 4-methylazulenyl group, a 2,4-dimethylazulenyl group, a 2-ethyl-4-azulenyl group, a 2-methyl-4-phenylhexahydroazulenyl group, a 2-methyl-4-isopropylazulenyl group, a 2,4,4-trimethylazulenyl group, a 4-methyl-4-hydroazulenyl group, a 2,4-dimethyl-4-hydroazulenyl group, a 2-methyl-4-(4-chlorophenyl)-4-hydroazulenyl group, a 2-methyl-4-phenyl-4-hydroazulenyl group, and a 2-methyl-4,4-diphenylazulenyl group, and substituted groups of the above groups.

Examples of the hetero atom contained in the above hetero atom-containing group of $L^1$ are an oxygen atom, a sulfur atom, a nitrogen atom, and a phosphorus atom. Examples of the hetero atom-containing group are an alkoxy group, an aryloxy group, a thioalkoxy group, a thioaryloxy group, an alkylamino group, an arylamino group, an alkylphosphino group, an arylphosphino group, an aromatic or aliphatic heterocyclic group containing an oxygen atom, a sulfur atom, a nitrogen atom, or a phosphorus atom in its ring, and a chelating ligand. Specific examples of the hetero atom-containing group are a methoxy group, an ethoxy group, a propoxy group, a butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-di-sec-butylphenoxy group, a 2-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a dipropylamino group, a diphenylamino group, an isopropylamino group, a tert-butylamino group, a pyrrolyl group, a dimethylphosphino group, a 2-(2-oxy-1-propyl)phenoxy group, a 1,2-benzenedioxy group, a 1,3-benzenedioxy group, a 4-isopropyl-1,2-benzenedioxy group, a 3-methoxy-1,2-benzenedioxy group, a 1,8-dihydroxynahpthyl group, a 1,2-dihydroxynahpthyl group, a 2,2'-biphenyldioxy group, a 1,1'-binaphthyl-2,2'-dioxy group, a 2,2'-dihydroxy-6,6'-dimethylbiphenyl group, a 4,4',6,6'-tetra-tert-butyl-2,2'-methylenediphenoxy group, and a 4,4',6,6'-tetramethyl-2,2'-isobutylidenediphenoxy group.

A further example of the above hetero atom-containing group of $L^1$ is a group represented by following formula [4]:

$(R^2)_3P=N---$ [4]

wherein the dashed line - - - is a bond to $M^1$; $R^2$ is a hydrogen atom, a halogen atom, or a hydrocarbyl group having 1 to 20 carbon atoms; three $R^2$s are the same as, or different from one another; and any two of three $R^2$s may be linked to each other to form a ring.

Examples of the halogen atom of $R^2$ are a fluorine atom, a chlorine atom, a bromine atom, an iodine atom. Examples of the hydrocarbyl group having 1 to 20 carbon atoms of $R^2$ are a methyl group, an ethyl group, a n-propyl group, an isopropyl group, a n-butyl group, a tert-butyl group, a cyclopropyl group, a cyclobutyl group, a cycloheptyl group, a cyclohexyl group, a phenyl group, a 1-naphthyl group, a 2-naphthyl group and a benzyl group.

A still further example of the above hetero atom-containing group of $L^1$ is a group represented by following formula [5]:

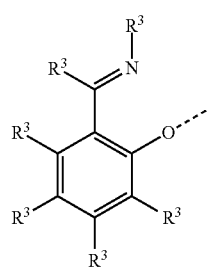

wherein the dashed line O - - - is a bond to $M^1$; $R^3$ is a hydrogen atom, a halogen atom, a hydrocarbyl group having 1 to 20 carbon atoms, a halogenated hydrocarbyl group having 1 to 20 carbon atoms, a hydrocarbyloxy group having 1 to 20 carbon atoms, a hydrocarbylsilyl group having 1 to 20 carbon atoms, a dihydrocarbylamino group having 2 to 20 carbon atoms, or a group derived from a heterocycle; six $R^3$s are the same as, or different from one another; and any two or more of six $R^3$s may be linked to one another to form a ring.

Examples of the halogen atom of $R^3$ are a fluorine atom, a chlorine atom, a bromine atom, and an iodine atom; examples of the hydrocarbyl group thereof are a phenyl group, a 1-naphthyl group, a 2-naphthyl group, a tert-butyl group, a 2,6-dimethylphenyl group, a 2-fluorenyl group, a 2-methylphenyl group, a 4-methoxyphenyl group, a cyclohexyl group, a 2-isopropylphenyl group, a benzyl group, a methyl group, a 1-methyl-1-phenylethyl group, and a 1,1-dimethylpropyl group; examples of the halogenated hydrocarbyl group thereof are a 4-trifluoromethylphenyl group and a 2-chlorophenyl group; an example of the hydrocarbyloxy group thereof is a methoxy group; examples of the hydrocarbylsilyl group thereof are a triethylsilyl group and a diphenylmethylsilyl group; an example of the dihydrocarbylamino group thereof is a dimethylamino group; and an example of the group derived from a heterocycle thereof is a 4-pyridyl group.

One more example of the above hetero atom-containing group of $L^1$ is a group represented by following formula [6]:

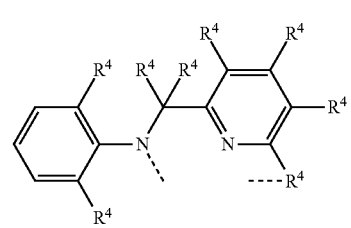

[6]

wherein two dashed lines N - - - and $R^4$ - - - are bonds to $M^1$; $R^4$ is a hydrogen atom, a halogen atom, a hydrocarbyl group having 1 to 20 carbon atoms, a halogenated hydrocarbyl group having 1 to 20 carbon atoms, a hydrocarbyloxy group having 1 to 20 carbon atoms, a hydrocarbylsilyl group having 1 to 20 carbon atoms, or a dihydrocarbylamino group having 2 to 20 carbon atoms; eight $R^4$s are the same as, or different from one another; and any two or more of eight $R^4$s may be linked to one another to form a ring.

Examples of the group represented by formula [6] are an N-(2,6-di(1-methylethyl)phenyl)amido)(o-tolyl)(α-naphthalene-2-diyl(6-pyridine-2-diyl)methane) group, an N-(2,6-di(1-methylethyl)phenyl)amido)(2-isopropylphenyl)(α-naphthalene-2-diyl(6-pyridine-2-diyl)methane) group, and an N-(2,6-di(1-methylethyl)phenyl)amido)(phenanthrene-5-yl)(α-naphthalene-2-diyl(6-pyridine-2-diyl)methane) group.

The above chelating ligand of the hetero atom-containing group means a ligand having two or more coordinating positions, such as acetylacetonate, diimine, oxazoline, bisoxazoline, terpyridine, acylhydrazone, diethylenetriamine, triethylenetetramine, porphyrin, crown ether and cryptate.

Examples of the linking group in above formula [3] are an alkylene group such as an ethylene group and a propylene group; a substituted alkylene group such as a dimethylmethylene group and a diphenylmethylene group; a silylene group; a substituted silylene group such as a dimethylsilylene group, a diphenylsilylene group, a tetramethyldisilylene group; and a hetero atom such as a nitrogen atom, an oxygen atom, a sulfur atom, and a phosphorus atom.

The above hydrocarbyl group and hydrocarbyloxy group having 1 to 20 carbon atoms of $X^1$ in formula [3] may have a substituent. Examples of the substituent are a halogen atom such as a fluorine atom, a chlorine atom, a bromine atom and an iodine atom; and a hydrocarbyloxy group such as an alkoxy group (for example, a methoxy group and an ethoxy group), an aryloxy group (for example, a phenoxy group), and an aralkyloxy group (for example, a benzyloxy group).

Examples of the above halogen atom of $X^1$ in formula [3] are a fluorine atom, a chlorine atom, a bromine atom and an iodine atom.

Examples of the above hydrocarbyl group having 1 to 20 carbon atoms of $X^1$ are an alkyl group having 1 to 20 carbon atoms, an aryl group having 6 to 20 carbon atoms, and an aralkyl group having 7 to 20 carbon atoms. Examples of the alkyl group having 1 to 20 carbon atoms are a methyl group, an ethyl group, a n-propyl group, an isopropyl group, a n-butyl group, a sec-butyl group, a tert-butyl group, an isobutyl group, a n-pentyl group, a neopentyl group, an amyl group, a n-hexyl group, a n-octyl group, a n-decyl group, a n-dodecyl group, a n-pentadecyl group and a n-eicosyl group. Among them, preferred is a methyl group, an ethyl group, an isopropyl group, a tert-butyl group, an isobutyl group, or an amyl group, more preferred is a methyl group, an ethyl group, or an isobutyl group, and further preferred is a methyl group. An example of the above aryl group having 6 to 20 carbon atoms is a phenyl group. An example of the above aralkyl group having 7 to 20 carbon atoms is a benzyl group.

Examples of the above hydrocarbyloxy group having 1 to 20 carbon atoms of $X^1$ are an alkoxy group having 1 to 20 carbon atoms such as a methoxy group, an ethoxy group, a n-propoxy group, an isopropoxy group, a n-butoxy group, and a tert-butoxy group; an aryloxy group having 6 to 20 carbon atoms such as a phenoxy group; and an aralkyloxy group having 7 to 20 carbon atoms such as a benzyloxy group.

$X^1$ in formula [3] is preferably a halogen atom, an aralkyl group having 7 to 20 carbon atoms, or an aryloxy group having 6 to 20 carbon atoms, and more preferably a chlorine atom, a benzyl group, or a phenoxy group.

When $M^1$ in formula [3] is a transition metal atom of group 4, "a" in formula [3] is preferably 4, and "b" therein is preferably 2.

Among transition metal compounds represented by formula [3], examples of the compound whose $M^1$ is a transition metal atom of group 4 are bis(cyclopentadienyl)titanium dichloride, bis(methylcyclopentadienyl)titanium dichloride, bis(n-butylcyclopentadienyl)titanium dichloride, bis(dimethylcyclopentadienyl)titanium dichloride, bis(ethylmethylcyclopentadienyl)titanium dichloride, bis(trimethylcyclopentadienyl)titanium dichloride, bis(tetramethylcyclopentadienyl)titanium dichloride, bis(pentamethylcyclopentadienyl)titanium dichloride, bis(indenyl)titanium dichloride, bis(4,5,6,7-tetrahydroindenyl)titanium dichloride, bis(fluorenyl)titanium dichloride, bis(2-phenylindenyl)titanium dichloride, bis[2-(bis-3,5-trifluoromethylphenyl)indenyl]titanium dichloride, bis[2-(4-tert-butylphenyl)indenyl]titanium dichloride, bis[2-(4-trifluoromethylphenyl)indenyl]titanium dichloride, bis[2-(4-methylphenyl)indenyl]titanium dichloride, bis[2-(3,5-dimethylphenyl)indenyl]titanium dichloride, bis[2-(pentafluorophenyl)indenyl]titanium dichloride, cyclopentadienyl(pentamethylcyclopentadienyl)titanium dichloride, cyclopentadienyl(indenyl)titanium dichloride, cyclopentadienyl(fluorenyl)titanium dichloride, indenyl(fluorenyl)titanium dichloride, pentamethylcyclopentadienyl(indenyl)titanium dichloride, pentamethylcyclopentadienyl(fluorenyl)titanium dichloride, cyclopentadienyl(2-phenylindenyl)titanium dichloride, pentamethylcyclopentadienyl(2-phenylindenyl)titanium dichloride, ethylenebis(cyclopentadienyl)titanium dichloride, ethylenebis(2-methylcyclopentadienyl)titanium dichloride, ethylenebis(3-methylcyclopentadienyl)titanium dichloride, ethylenebis(2-n-butylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl)titanium dichloride, ethylenebis(2,5-dimethylcyclopentadienyl)titanium dichloride, ethylenebis(3,4-dimethylcyclopentadienyl)titanium dichloride, ethylenebis(2,3-ethylmethylcyclopentadienyl)titanium dichloride, ethylenebis(2,4-ethylmethylcyclopentadienyl)titanium dichloride, ethylenebis(2,5-ethylmethylcyclopentadienyl)titanium dichloride, ethylenebis(3,5-ethylmethylcyclopentadienyl)titanium dichloride, ethylenebis(2,3,4-trimethylcyclopentadienyl)titanium dichloride, ethylenebis(2,3,5-trimethylcyclopentadienyl)titanium dichloride, ethylenebis(tetramethylcyclopentadienyl)titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(fluorenyl)titanium dichloride, ethylene(cyclopentadienyl)(pentamethylcyclopentadienyl)titanium dichloride, ethylene(cyclopentadienyl)(indenyl)titanium dichloride, ethylene(methylcyclopentadienyl)(indenyl)titanium dichloride, ethylene(n-butylcyclopentadienyl)(indenyl)titanium dichloride, ethylene(tetramethylcyclopentadienyl)(indenyl)titanium dichloride, ethylene(cyclopentadienyl)(fluorenyl)titanium dichloride, ethylene(methylcyclopentadienyl)(fluorenyl)titanium dichloride, ethylene(pentamethylcyclopentadienyl)(fluorenyl)titanium dichloride, ethylene(n-butylcyclopentadienyl)(fluorenyl)titanium dichloride, ethylene (tetramethylpentadienyl)(fluorenyl)titanium dichloride, ethylene(indenyl)(fluorenyl)titanium dichloride, isopropylidenebis(cyclopentadienyl)titanium dichloride, isopropylidenebis(2-methylcyclopentadienyl)titanium dichloride, isopropylidenebis(3-methylcyclopentadienyl)titanium dichloride, isopropylidenebis(2-n-butylcyclopentadienyl)titanium dichloride, isopropylidenebis(3-n-butylcyclopentadienyl)titanium dichloride, isopropylidenebis(2,3-dimethylcyclopentadienyl) titanium dichloride, isopropylidenebis(2,4-dimethylcyclopentadienyl)titanium dichloride, isopropylidenebis(2,5-dimethylcyclopentadienyl) titanium dichloride, isopropylidenebis(3,4-dimethylcyclopentadienyl)titanium dichloride, isopropylidenebis(2,3-ethylmethylcyclopentadienyl)titanium dichloride, isopropylidenebis(2,4-ethylmethylcyclopentadienyl)titanium dichloride, isopropylidenebis(2,5-ethylmethylcyclopentadienyl)titanium dichloride, isopropylidenebis(3,5-ethylmethylcyclopentadienyl)titanium dichloride, isopropylidenebis(2,3,4-trimethylcyclopentadienyl)titanium dichloride, isopropylidenebis(2,3,5-trimethylcyclopentadienyl)titanium dichloride, isopropylidenebis(tetramethylcyclopentadienyl)titanium dichloride, isopropylidenebis(indenyl)titanium dichloride, isopropylidenebis(4,5,6,7-tetrahydroindenyl)titanium dichloride, isopropylidenebis(2-phenylindenyl)titanium dichloride, isopropylidenebis(fluorenyl)titanium dichloride, isopropylidene(cyclopentadienyl)(tetramethylcyclopentadienyl)titanium dichloride, isopropylidene(cyclopentadienyl)(indenyl)titanium dichloride, isopropylidene(methylcyclopentadienyl)(indenyl)titanium dichloride, isopropylidene(n-butylcyclopentadienyl)(indenyl)titanium dichloride, isopropylidene(tetramethylcyclopentadienyl)(indenyl)titanium dichloride, isopropylidene (cyclopentadienyl)(fluorenyl)titanium dichloride, isopropylidene(methylcyclopentadienyl)(fluorenyl)titanium dichloride, isopropylidene(n-butylcyclopentadienyl)(fluorenyl)titanium dichloride, isopropylidene(tetramethylcyclopentadienyl)(fluorenyl)titanium dichloride, isopropylidene(indenyl)(fluorenyl)titanium dichloride, dimethylsilylenebis(cyclopentadienyl)titanium dichloride, dimethylsilylenebis(2-methylcyclopentadienyl) titanium dichloride, dimethylsilylenebis(3-methylcyclopentadienyl)titanium dichloride, dimethylsilylenebis(2-n-butylcyclopentadienyl)titanium dichloride, dimethylsilylenebis(3-n-butylcyclopentadienyl)titanium dichloride, dimethylsilylenebis(2,3-dimethylcyclopentadienyl)titanium dichloride, dimethylsilylenebis(2,4-dimethylcyclopentadienyl)titanium dichloride, dimethylsilylenebis(2,5-dimethylcyclopentadienyl)titanium dichloride, dimethylsilylenebis(3,4-dimethylcyclopentadienyl)titanium dichloride, dimethylsilylenebis(2,3-ethylmethylcyclopentadienyl)titanium dichloride, dimethylsilylenebis(2,4-ethylmethylcyclopentadienyl)titanium dichloride, dimethylsilylenebis(2,5-ethylmethylcyclopentadienyl)titanium dichloride, dimethylsilylenebis(3,5-ethylmethylcyclopentadienyl)titanium dichloride, dimethylsilylenebis(2,3,4-trimethylcyclopentadienyl)titanium dichloride, dimethylsilylenebis(2,3,5-trimethylcyclopentadienyl)titanium dichloride, dimethylsilylenebis(tetramethylcyclopentadienyl)titanium dichloride, dimethylsilylenebis(indenyl)titanium dichloride, dimethylsilylenebis(4,5,6,7-tetrahydroindenyl)titanium dichloride, dimethylsilylene(cyclopentadienyl)(indenyl)titanium dichloride, dimethylsilylene(methylcyclopentadienyl)(indenyl)titanium dichloride, dimethylsilylene(n-butylcyclopentadienyl)(indenyl)titanium dichloride, dimethylsilylene(tetramethylcyclopentadienyl)(indenyl)titanium dichloride, dimethylsilylene(cyclopentadienyl)(fluorenyl)titanium dichloride, dimethylsilylene(methylcyclopentadienyl)(fluorenyl)titanium dichloride, dimethylsilylene(n-butylcyclopentadienyl)(fluorenyl)titanium dichloride, dimethylsilylene(tetramethylcyclopentadienyl)(fluorenyl)titanium dichloride, dimethylsilylene(indenyl)(fluorenyl)titanium dichloride; cyclopentadienyltitanium trichloride, pentamethylcyclopentadienyltitanium trichloride, cyclopentadienyl(dimethylamido)titanium dichloride, cyclopentadienyl(phenoxy)titanium dichloride, cyclopentadienyl(2,6-dimethylphenyl)titanium dichloride, cyclopentadienyl(2,6-diisopropylphenyl)titanium dichloride, cyclopentadienyl(2,6-di-tert-butylphenyl)titanium dichloride, pentamethylcyclopentadienyl(2,6-dimethylphenyl)titanium dichloride, pentamethylcyclopentadienyl(2,6-diisopropylphenyl)titanium dichloride, pentamethylcyclopentadienyl(2,6-di-tert-butylphenyl)titanium dichloride, indenyl(2,6-diisopropylphenyl)titanium dichloride, fluorenyl(2,6-diisopropylphenyl)titanium dichloride, methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy) titanium dichloride, methylene(methylcyclopentadienyl)(3-tert-butyl-5-methyl-2-phenoxy)titanium dichloride, methylene(methylcyclopentadienyl)(3-phenyl-2-phenoxy) titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene (methylcyclopentadienyl)(3-tert-butyl-5-methoxy-2-phenoxy)titanium dichloride, methylene (methylcyclopentadienyl)(3-tert-butyl-5-chloro-2-phenoxy) titanium dichloride, methylene(tert-butylcyclopentadienyl) (3,5-dimethyl-2-phenoxy)titanium dichloride, methylene (tert-butylcyclopentadienyl)(3-tert-butyl-2-phenoxy) titanium dichloride, methylene(tert-butylcyclopentadienyl) (3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethyl silyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene (tetramethylcyclopentadienyl)(3-phenyl-2-phenoxy)titanium dichloride, methylene(tetramethylcyclopentadienyl)(3-tert-butyldimethyl silyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene (tetramethylcyclopentadienyl)(3-tert-butyl-5-chloro-2-phenoxy)titanium dichloride, methylene (trimethylsilylcyclopentadienyl)(3,5-dimethyl-2-phenoxy) titanium dichloride, methylene (trimethylsilylcyclopentadienyl)(3-tert-butyl-2-phenoxy) titanium dichloride, methylene (trimethylsilylcyclopentadienyl)(3-tert-butyl-5-methyl-2-phenoxy)titanium dichloride, methylene (trimethylsilylcyclopentadienyl)(3-phenyl-2-phenoxy) titanium dichloride, methylene (trimethylsilylcyclopentadienyl)(3-tert-butyl dimethylsilyl-5-methyl-2-phenoxy)titanium dichloride, methylene (trimethylsilylcyclopentadienyl)(3-trimethylsilyl-5-methyl-2-phenoxy)titanium dichloride, methylene (trimethylsilylcyclopentadienyl)(3-tert-butyl-5-methoxy-2-phenoxy)titanium dichloride, methylene (trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene (fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy) titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy) titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy) titanium dichloride, isopropylidene(cyclopentadienyl)(3-tert-butyl-2-phenoxy)titanium dichloride, isopropylidene (cyclopentadienyl)(3-tert-butyl-5-methyl-2-phenoxy)

titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene (cyclopentadienyl)(3-trimethylsilyl-5-methyl-2-phenoxy) titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene (methylcyclopentadienyl)(3-tert-butyldimethyl silyl-5-methyl-2-phenoxy)titanium dichloride, isopropylidene(methylcyclopentadienyl)(3-trimethylsilyl-5-methyl-2-phenoxy)titanium dichloride, isopropylidene (methylcyclopentadienyl)(3-tert-butyl-5-methoxy-2-phenoxy)titanium dichloride, isopropylidene (methylcyclopentadienyl)(3-tert-butyl-5-chloro-2-phenoxy) titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene (tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyl dimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene (tert-butylcyclopentadienyl)(3-tert-butyl-5-chloro-2-phenoxy)titanium dichloride, isopropylidene (tetramethylcyclopentadienyl)(3,5-dimethyl-2-phenoxy) titanium dichloride, isopropylidene (tetramethylcyclopentadienyl)(3-tert-butyl-2-phenoxy) titanium dichloride, isopropylidene (tetramethylcyclopentadienyl)(3-tert-butyl-5-methyl-2-phenoxy)titanium dichloride, isopropylidene (tetramethylcyclopentadienyl) (3-phenyl-2-phenoxy) titanium dichloride, isopropylidene (tetramethylcyclopentadienyl)(3-tert-butyl dimethylsilyl-5-methyl-2-phenoxy)titanium dichloride, isopropylidene (tetramethylcyclopentadienyl)(3-trimethyl silyl-5-methyl-2-phenoxy)titanium dichloride, isopropylidene (tetramethylcyclopentadienyl)(3-tert-butyl-5-methoxy-2-phenoxy)titanium dichloride, isopropylidene (tetramethylcyclopentadienyl)(3-tert-butyl-5-chloro-2-phenoxy)titanium dichloride, isopropylidene (trimethylsilylcyclopentadienyl)(3,5-dimethyl-2-phenoxy) titanium dichloride, isopropylidene (trimethylsilylcyclopentadienyl)(3-tert-butyl-2-phenoxy) titanium dichloride, isopropylidene (trimethylsilylcyclopentadienyl)(3-tert-butyl-5-methyl-2-phenoxy)titanium dichloride, isopropylidene (trimethylsilylcyclopentadienyl)(3-phenyl-2-phenoxy) titanium dichloride, isopropylidene (trimethylsilylcyclopentadienyl)(3-tert-butyl dimethylsilyl-5-methyl-2-phenoxy)titanium dichloride, isopropylidene (trimethylsilylcyclopentadienyl)(3-trimethyl silyl-5-methyl-2-phenoxy)titanium dichloride, isopropylidene (trimethylsilylcyclopentadienyl)(3-tert-butyl-5-methoxy-2-phenoxy)titanium dichloride, isopropylidene (trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene (fluorenyl)(3-tert-butyl-2-phenoxy)titanium dichloride, isopropylidene(fluorenyl)(3-tert-butyl-5-methyl-2-phenoxy) titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy) titanium dichloride, diphenylmethylene(cyclopentadienyl) (3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethyl silyl-5-methyl-2-phenoxy)titanium dichloride, diphenylmethylene(cyclopentadienyl)(3-trimethylsilyl-5-methyl-2-phenoxy)titanium dichloride, diphenylmethylene (cyclopentadienyl)(3-tert-butyl-5-methoxy-2-phenoxy)titanium dichloride; diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyl dimethylsilyl-5-methyl-2-phenoxy)titanium dichloride, diphenylmethylene (methylcyclopentadienyl)(3-trimethylsilyl-5-methyl-2-phenoxy)titanium dichloride, diphenylmethylene (methylcyclopentadienyl)(3-tert-butyl-5-methoxy-2-phenoxy)titanium dichloride, diphenylmethylene (methylcyclopentadienyl)(3-tert-butyl-5-chloro-2-phenoxy) titanium dichloride, diphenylmethylene(tert-butylcyclopentadienyl)(3,5-dimethyl-2-phenoxy)titanium dichloride, diphenylmethylene(tert-butylcyclopentadienyl) (3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl) (3-tert-butyl dimethylsilyl-5-methyl-2-phenoxy)titanium dichloride, diphenylmethylene(tert-butylcyclopentadienyl) (3-trimethyl silyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene (tetramethylcyclopentadienyl)(3,5-dimethyl-2-phenoxy) titanium dichloride, diphenylmethylene (tetramethylcyclopentadienyl)(3-tert-butyl-2-phenoxy) titanium dichloride, diphenylmethylene (tetramethylcyclopentadienyl)(3-tert-butyl-5-methyl-2-phenoxy)titanium dichloride, diphenylmethylene (tetramethylcyclopentadienyl)(3-phenyl-2-phenoxy) titanium dichloride, diphenylmethylene (tetramethylcyclopentadienyl)(3-tert-butyl dimethylsilyl-5-methyl-2-phenoxy)titanium dichloride, diphenylmethylene (tetramethylcyclopentadienyl)(3-trimethyl silyl-5-methyl-2-phenoxy)titanium dichloride, diphenylmethylene (tetramethylcyclopentadienyl)(3-tert-butyl-5-methoxy-2- phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titanium dichloride, dimethylsilylene(cyclopentadienyl)(2-phenoxy)titanium dichloride, dimethylsilylene(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsily1-5-methyl-2-phenoxy)titanium dichloride, dimethylsilylene(cyclopentadienyl)(5-methyl-3-trimethylsilyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy)titanium dichloride, dimethylsilylene(methylcyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(methylcyclopentadienyl)(3-tert-butyl-5-methoxy-2-phenoxy)titanium dichloride, dimethylsilylene(methylcyclopentadienyl)(3-tert-butyl-5-chloro-2-phenoxy)titanium dichloride, dimethylsilylene(methylcyclopentadienyl)(3,5-diamyl-2-phenoxy)titanium dichloride, dimethylsilylene(n-butylcyclopentadienyl)(2-phenoxy)titanium dichloride, dimethylsilylene(n-butylcyclopentadienyl)(3-methyl-2-phenoxy)titanium dichloride, dimethylsilylene(n-butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy)titanium dichloride, dimethylsilylene(n-butylcyclopentadienyl)(5-methyl-3-phenyl-2-phenoxy)titanium dichloride, dimethylsilylene(n-butylcyclopentadienyl)(3-tert-butyl dimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy)titanium dichloride, dimethylsilylene(n-butylcyclopentadienyl)(3-tert-butyl-5-chloro-2-phenoxy)titanium dichloride, dimethylsilylene(n-butylcyclopentadienyl)(3,5-diamyl-2-phenoxy)titanium dichloride, dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy)titanium dichloride, dimethylsilylene(tert-butylcyclopentadienyl)(3,5-di-tert-butyl-2-phenoxy)titanium dichloride, dimethylsilylene(tert-butylcyclopentadienyl)(5-methyl-3-phenyl-2-phenoxy)titanium dichloride, dimethylsilylene(tert-butylcyclopentadienyl)(3-tert-butyl dimethylsilyl-5-methyl-2-phenoxy)titanium dichloride, dimethylsilylene(tert-butylcyclopentadienyl)(5-methyl-3-trimethylsilyl-2-phenoxy)titanium dichloride, dimethylsilylene(tert-butylcyclopentadienyl)(3-tert-butyl-5-methoxy-2-phenoxy)titanium dichloride, dimethylsilylene(tert-butylcyclopentadienyl)(3-tert-butyl-5-chloro-2-phenoxy)titanium dichloride, dimethylsilylene(tert-butylcyclopentadienyl)(3,5-diamyl-2-phenoxy)titanium dichloride, dimethylsilylene(tetramethylcyclopentadienyl)(2-phenoxy)titanium dichloride, dimethylsilylene(tetramethylcyclopentadienyl)(3-methyl-2-phenoxy)titanium dichloride, dimethylsilylene(tetramethylcyclopentadienyl)(3,5-dimethyl-2-phenoxy)titanium dichloride, dimethylsilylene(tetramethylcyclopentadienyl)(3-tert-butyl-2-phenoxy)titanium dichloride, dimethylsilylene(tetramethylcyclopentadienyl)(3-tert-butyl-5-methyl-2-phenoxy)titanium dichloride, dimethylsilylene(tetramethylcyclopentadienyl)(3,5-di-tert-butyl-2-phenoxy)titanium dichloride, dimethylsilylene(tetramethylcyclopentadienyl)(5-methyl-3-phenyl-2-phenoxy)titanium dichloride, dimethylsilylene(tetramethylcyclopentadienyl)(3-tert-butyl dimethylsilyl-5-methyl-2-phenoxy)titanium dichloride, dimethylsilylene(tetramethylcyclopentadienyl)(5-methyl-3-trimethylsilyl-2-phenoxy)titanium dichloride, dimethylsilylene(tetramethylcyclopentadienyl)(3-tert-butyl-5-methoxy-2-phenoxy)titanium dichloride, dimethylsilylene(tetramethylcyclopentadienyl)(3-tert-butyl-5-chloro-2-phenoxy)titanium dichloride, dimethylsilylene(tetramethylcyclopentadienyl)(3,5-diamyl-2-phenoxy)titanium dichloride, dimethylsilylene (trimethylsilylcyclopentadienyl)(2-phenoxy)titanium dichloride, dimethylsilylene(trimethylsilylcyclopentadienyl)(3-methyl-2-phenoxy)titanium dichloride, dimethylsilylene(trimethylsilylcyclopentadienyl)(3,5-dimethyl-2-phenoxy)titanium dichloride, dimethylsilylene(trimethylsilylcyclopentadienyl)(3-tert-butyl-2-phenoxy)titanium dichloride, dimethylsilylene(trimethylsilylcyclopentadienyl)(3-tert-butyl-5-methyl-2-phenoxy)titanium dichloride, dimethylsilylene(trimethylsilylcyclopentadienyl)(3,5-di-tert-butyl-2-phenoxy)titanium dichloride, dimethylsilylene(trimethylsilylcyclopentadienyl)(5-methyl-3-phenyl-2-phenoxy)titanium dichloride, dimethylsilylene(trimethylsilylcyclopentadienyl)(3-tert-butyldimethylsilyl-5-methyl-2-phenoxy)titanium dichloride, dimethylsilylene(trimethylsilylcyclopentadienyl)(5-methyl-3-trimethylsilyl-2-phenoxy)titanium dichloride, dimethylsilylene(trimethylsilylcyclopentadienyl)(3-tert-butyl-5-methoxy-2-phenoxy)titanium dichloride, dimethylsilylene(trimethylsilylcyclopentadienyl)(3-tert-butyl-5-chloro-2-phenoxy)titanium dichloride, dimethylsilylene(trimethylsilylcyclopentadienyl)(3,5-diamyl-2-phenoxy)titanium dichloride, dimethylsilylene(indenyl)(2-phenoxy)titanium dichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl)(3,5-di-tert-butyl-2-phenoxy)titanium dichloride, dimethylsilylene(indenyl)(5-methyl-3-phenyl-2-phenoxy)titanium dichloride, dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy)titanium dichloride, dimethylsilylene(indenyl)(3,5-diamyl-2-phenoxy)titanium dichloride, dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy)titanium dichloride, dimethylsilylene(fluorenyl)(3-tert-butyl-5-methyl-2-phenoxy)titanium dichloride, dimethylsilylene(fluorenyl)(3,5-di-tert-butyl-2-phenoxy)titanium dichloride, dimethylsilylene(fluorenyl)(5-methyl-3-phenyl-2-phenoxy)titanium dichloride, dimethylsilylene(fluorenyl)(3-tert-butyldimethylsilyl-5-methyl-2-phenoxy)titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-diamyl-2-phenoxy)titanium dichloride, dimethylsilylene(tetramethylcyclopentadienyl)(1-naphthoxy-2-yl)titanium dichloride, cyclopentylidene(cyclopentadienyl)(3,6-di-tert-butylfluorenyl)titanium dichloride, cyclohexylidene(cyclopentadienyl)(3,6-di-tert-butylfluorenyl)titanium dichloride, adamantylidene(cyclopentadienyl)(3,6-di-tert-butylfluorenyl)titanium dichloride, monophenylmonomethylmethylene(cyclopentadienyl)(3,6-di-tert-butylfluorenyl)titanium dichloride, dimethylmethylene(cyclopentadienyl)(3,6-di-tert-butylfluorenyl)titanium dichloride, diphenylmethylene(cyclopentadienyl)(3,6-di-tert-butylfluorenyl)titanium dichloride, di(p-tolyl)methylene(cyclopentadienyl)(3,6-di-tert-butylfluorenyl)titanium dichloride, diethylmethylene(cyclopentadienyl)(3,6-di-tert-butylfluorenyl)titanium dichloride, cyclopentylidene(cyclopentadienyl)(2,7-di-tert-butylfluorenyl)titanium dichloride, cyclohexylidene(cyclopentadienyl)(2,7-di-tert-butylfluorenyl)titanium dichloride, adamantylidene(cyclopentadienyl)(2,7-di-tert-butylfluorenyl)titanium dichloride, monophenylmonomethylmethylene(cyclopentadienyl)(2,7-di-tert-butylfluorenyl)titanium dichloride, dimethylmethylene(cyclopentadienyl)(2,7-di-tert-butylfluorenyl)titanium dichloride, diphenylmethylene(cyclopentadienyl)(2,7-di-tert-butylfluorenyl)titanium dichloride, di(p-tolyl)methylene(cyclopentadienyl)(2,7-di-tert-butylfluorenyl)titanium dichloride, diethylmethylene(cyclopentadienyl)(2,7-di-tert-butylfluorenyl)titanium dichloride, cyclopentylidene(cyclopentadienyl)(2,7-dicumylfluorenyl)titanium dichloride, cyclohexylidene(cyclopentadienyl)(2,7-dicumylfluorenyl)titanium dichloride, adamantylidene(cyclopentadienyl)(2,7-dicumylfluorenyl)titanium dichloride, monophenylmonomethylmethylene(cyclopentadienyl)(2,7-dicumylfluorenyl)titanium dichloride, dimethylmethylene(cyclopentadienyl)(2,7-dicumylfluorenyl)titanium dichloride, diphenylmethylene(cyclopentadienyl)(2,7-dicumylfluorenyl)titanium dichloride, di(p-tolyl)methylene(cyclopentadienyl)(2,7-dicumylfluorenyl)titanium dichloride, diethylmethylene(cyclopentadienyl)(2,7-dicumylfluorenyl)titanium dichloride, cyclopentylidene(cyclopentadienyl)(3,6-dicumylfluorenyl)titanium dichloride, cyclohexylidene(cyclopentadienyl)(3,6-dicumylfluorenyl)titanium dichloride, adamantylidene(cyclopentadienyl)(3,6-dicumylfluorenyl)titanium dichloride, monophenylmonomethylmethylene(cyclopentadienyl)(3,6-dicumylfluorenyl)titanium dichloride, dimethylmethylene(cyclopentadienyl)(3,6-dicumylfluorenyl)titanium dichloride, diphenylmethylene(cyclopentadienyl)(3,6-dicumylfluorenyl)titanium dichloride, di(p-tolyl)methylene(cyclopentadienyl)(3,6-dicumylfluorenyl)titanium dichloride, diethylmethylene(cyclopentadienyl)(3,6-dicumylfluorenyl)titanium dichloride, cyclopentylidene(cyclopentadienyl)(2,7-dimethylfluorenyl)titanium dichloride, cyclohexylidene(cyclopentadienyl)(2,7-dimethylfluorenyl)titanium dichloride, adamantylidene(cyclopentadienyl)(2,7-dimethylfluorenyl)titanium dichloride, monophenylmonomethylmethylene(cyclopentadienyl)(2,7-dimethylfluorenyl)titanium dichloride, dimethylmethylene(cyclopentadienyl)(2,7-dimethylfluorenyl)titanium dichloride, diphenylmethylene(cyclopentadienyl)(2,7-dimethylfluorenyl)titanium dichloride, di(p-tolyl)methylene(cyclopentadienyl)(2,7-dimethylfluorenyl)titanium dichloride, diethylmethylene(cyclopentadienyl)(2,7-dimethylfluorenyl)titanium dichloride, cyclopentylidene(cyclopentadienyl)(3,6-dimethylfluorenyl)titanium dichloride, cyclohexylidene(cyclopentadienyl) (3,6-dimethylfluorenyl)titanium dichloride, adamantylidene(cyclopentadienyl)(3,6-dimethylfluorenyl)titanium dichloride, monophenylmonomethylmethylene(cyclopentadienyl)(3,6-dimethylfluorenyl)titanium dichloride, dimethylmethylene(cyclopentadienyl)(3,6-dimethylfluorenyl)titanium dichloride, diphenylmethylene(cyclopentadienyl)(3,6-dimethylfluorenyl)titanium dichloride, di(p-tolyl)methylene(cyclopentadienyl)(3,6-dimethylfluorenyl)titanium dichloride, diethylmethylene(cyclopentadienyl)(3,6-dimethylfluorenyl)titanium dichloride, cyclopentylidene(cyclopentadienyl)(2,7-diphenylfluorenyl)titanium dichloride, cyclohexylidene(cyclopentadienyl)(2,7-diphenylfluorenyl)titanium dichloride, adamantylidene(cyclopentadienyl)(2,7-diphenylfluorenyl)titanium dichloride, monophenylmonomethylmethylene(cyclopentadienyl)(2,7-diphenylfluorenyl)titanium dichloride, dimethylmethylene(cyclopentadienyl)(2,7-diphenylfluorenyl)titanium dichloride, diphenylmethylene(cyclopentadienyl)(2,7-diphenylfluorenyl)titanium dichloride, di(p-tolyl)methylene(cyclopentadienyl)(2,7-diphenylfluorenyl)titanium dichloride, diethylmethylene(cyclopentadienyl)(2,7-diphenylfluorenyl)titanium dichloride, cyclopentylidene(cyclopentadienyl)(3,6-diphenylfluorenyl)titanium dichloride, cyclohexylidene(cyclopentadienyl)(3,6-diphenylfluorenyl)titanium dichloride, adamantylidene(cyclopentadienyl)(3,6-diphenylfluorenyl)titanium dichloride, monophenylmonomethylmethylene(cyclopentadienyl)(3,6-diphenylfluorenyl)titanium dichloride, dimethylmethylene(cyclopentadienyl)(3,6-diphenylfluorenyl)titanium dichloride, diphenylmethylene(cyclopentadienyl)(3,6-diphenylfluorenyl)titanium dichloride, di(p-tolyl)methylene(cyclopentadienyl)(3,6-diphenylfluorenyl)titanium dichloride, diethylmethylene(cyclopentadienyl)(3,6-diphenylfluorenyl)titanium dichloride, cyclopentylidene(cyclopentadienyl)(2,7-di(2,4,6-trimethylphenyl)fluorenyl)titanium dichloride, cyclohexylidene(cyclopentadienyl)(2,7-di(2,4,6-trimethylphenyl)fluorenyl)titanium dichloride, adamantylidene(cyclopentadienyl)(2,7-di(2,4,6-trimethylphenyl)fluorenyl)titanium dichloride, monophenylmonomethylmethylene(cyclopentadienyl)(2,7-di(2,4,6-trimethylphenyl)fluorenyl)titanium dichloride, dimethylmethylene(cyclopentadienyl)(2,7-di(2,4,6-trimethylphenyl)fluorenyl)titanium dichloride, diphenylmethylene(cyclopentadienyl)(2,7-di(2,4,6-trimethylphenyl)fluorenyl)titanium dichloride, di(p-tolyl)methylene(cyclopentadienyl)(2,7-di(2,4,6-trimethylphenyl)fluorenyl)titanium dichloride, diethylmethylene(cyclopentadienyl)(2,7-di(2,4,6-trimethylphenyl)fluorenyl)titanium dichloride, cyclopentylidene(cyclopentadienyl)(3,6-di(2,4,6-trimethylphenyl)fluorenyl)titanium dichloride, cyclohexylidene(cyclopentadienyl)(3,6-di(2,4,6-trimethylphenyl)fluorenyl)titanium dichloride, adamantylidene(cyclopentadienyl)(3,6-di(2,4,6-trimethylphenyl)fluorenyl)titanium dichloride, monophenylmonomethylmethylene(cyclopentadienyl)(3,6-di(2,4,6-trimethylphenyl)fluorenyl)titanium dichloride, dimethylmethylene(cyclopentadienyl)(3,6-di(2,4,6-trimethylphenyl)fluorenyl)titanium dichloride, diphenylmethylene(cyclopentadienyl)(3,6-di(2,4,6-trimethylphenyl)fluorenyl)titanium dichloride, di(p-tolyl)methylene(cyclopentadienyl)(3,6-di(2,4,6-trimethylphenyl)fluorenyl)titanium dichloride, diethylmethylene(cyclopentadienyl)(3,6-di(2,4,6-trimethylphenyl)fluorenyl)titanium dichloride, cyclopentylidene(cyclopentadienyl)(2,7-diisopropyl fluorenyl)titanium dichloride, cyclohexylidene(cyclopentadienyl)(2,7-diisopropylfluorenyl)titanium dichloride, adamantylidene(cyclopentadienyl)(2,7-diisopropylfluorenyl)titanium dichloride, monophenylmonomethylmethylene(cyclopentadienyl)(2,7-diisopropylfluorenyl)titanium dichloride, dimethylmethylene(cyclopentadienyl)(2,7-diisopropylfluorenyl)titanium dichloride, diphenylmethylene(cyclopentadienyl)(2,7-diisopropylfluorenyl)titanium dichloride, di(p-tolyl)methylene(cyclopentadienyl)(2,7-diisopropylfluorenyl)titanium dichloride, diethylmethylene(cyclopentadienyl)(2,7-diisopropylfluorenyl)titanium dichloride, cyclopentylidene(cyclopentadienyl)(3,6-diisopropylfluorenyl)titanium dichloride, cyclohexylidene(cyclopentadienyl)(3,6-diisopropylfluorenyl)titanium dichloride, adamantylidene(cyclopentadienyl)(3,6-diisopropylfluorenyl)titanium dichloride, monophenylmonomethylmethylene(cyclopentadienyl)(3,6-diisopropylfluorenyl)titanium dichloride, dimethylmethylene(cyclopentadienyl)(3,6-diisopropylfluorenyl)titanium dichloride, diphenylmethylene(cyclopentadienyl)(3,6-diisopropylfluorenyl)titanium dichloride, di(p-tolyl)methylene(cyclopentadienyl)(3,6-diisopropylfluorenyl)titanium dichloride, diethylmethylene(cyclopentadienyl)(3,6-diisopropylfluorenyl)titanium dichloride, cyclopentylidene(cyclopentadienyl)(2,7-dicyclohexylfluorenyl)titanium dichloride, cyclohexylidene(cyclopentadienyl)(2,7-dicyclohexylfluorenyl)titanium dichloride, adamantylidene(cyclopentadienyl)(2,7-dicyclohexylfluorenyl)titanium dichloride, monophenylmonomethylmethylene(cyclopentadienyl)(2,7-dicyclohexylfluorenyl)titanium dichloride, dimethylmethylene(cyclopentadienyl)(2,7-dicyclohexylfluorenyl)titanium dichloride, diphenylmethylene(cyclopentadienyl)(2,7-dicyclohexylfluorenyl)titanium dichloride, di(p-tolyl)methylene(cyclopentadienyl)(2,7-dicyclohexylfluorenyl)titanium dichloride, diethylmethylene(cyclopentadienyl)(2,7-dicyclohexylfluorenyl)titanium dichloride, cyclopentylidene(cyclopentadienyl)(3,6-dicyclohexylfluorenyl)titanium dichloride, cyclohexylidene(cyclopentadienyl)(3,6-dicyclohexylfluorenyl)titanium dichloride, adamantylidene(cyclopentadienyl)(3,6-dicyclohexylfluorenyl)titanium dichloride, monophenylmonomethylmethylene(cyclopentadienyl)(3,6-dicyclohexylfluorenyl)titanium dichloride, dimethylmethylene(cyclopentadienyl)(3,6-dicyclohexylfluorenyl)titanium dichloride, diphenylmethylene(cyclopentadienyl)(3,6-dicyclohexylfluorenyl)titanium dichloride, di(p-tolyl)methylene(cyclopentadienyl)(3,6-dicyclohexylfluorenyl)titanium dichloride, diethylmethylene(cyclopentadienyl)(3,6-dicyclohexylfluorenyl)titanium dichloride, isopropylidene(3-tert-butylcyclopentadienyl)(2-methyl-4-phenylazulenyl)titanium dichloride, methylenebis(2-methyl-4-phenylazulenyl)titanium dichloride, ethylenebis(4-methylazulenyl)titanium dichloride, ethylenebis(2,4-dimethylazulenyl)titanium dichloride, ethylenebis(2-methyl-4-phenylazulenyl)titanium dichloride, ethylenebis(2-ethyl-4-phenylazulenyl)titanium dichloride, ethylenebis(2-methyl-4-phenylhexahydroazulenyl)titanium dichloride, ethylenebis(2-methyl-4-isopropylazulenyl)titanium dichloride, cyclohexylidenebis(2,4,4-trimethylazulenyl)titanium dichloride, dimethylsilylenebis(4-methyl-4-hydroazulenyl)titanium dichloride, dimethylsilylenebis(2,4-dimethyl-4-hydroazulenyl)titanium dichloride, dimethylsilylenebis[1,1'-{2-methyl-4-(4-chlorophenyl)-4-hydroazulenyl}]titanium dichloride, dimethylsilylenebis{1,1'-(2-methyl-4-phenyl-4-hydroazulenyl)}titanium dichloride, dimethylsilylenebis(2-methyl-4-phenylazulenyl)titanium dichloride, dimethylsilylenebis(2-methyl-4-phenylhexahydroazulenyl)titanium dichloride, dimethylsilylenebis(2-methyl-4,4-diphenylazulenyl)titanium dichloride, dimethylsilylenebis(2-methyl-4-isopropylazulenyl)titanium dichloride, phenylmethylsilylenebis(2,4,4-trimethylazulenyl)titanium dichloride, (tert-butylamido)tetramethylcyclopentadienyl-1,2-ethanediyl titanium dichloride, (tert-butylamido)tetramethylcyclopentadienyl-1,2-ethanediyl titanium dimethyl, (tert-butylamido)tetramethylcyclopentadienyl-1,2-ethanediyl titanium dibenzyl, (methylamido)tetramethylcyclopentadienyl-1,2-ethanediyl titanium dichloride, (ethylamido)tetramethylcyclopentadienyl-1,2-ethanediyl titanium dichloride, (tert-butylamido)tetramethylcyclopentadienyldimethylsilane titanium dichloride, (tert-butylamido)tetramethylcyclopentadienyldimethylsilane titanium dimethyl, (tert-butylamido)tetramethylcyclopentadienyldimethylsilane titanium dibenzyl, (benzylamido)tetramethylcyclopentadienyldimethylsilane titanium dichloride, (phenylphosphido)tetramethylcyclopentadienyldimethylsilane titanium dibenzyl, (tert-butylamido)indenyl-1,2-ethanediyltitanium dichloride, (tert-butylamido)indenyl-1,2-ethanediyltitanium dimethyl, (tert-butylamido)tetrahydroindenyl-1,2-ethanediyltitanium dichloride, (tert-butylamido)tetrahydroindenyl-1,2-ethanediyltitanium dimethyl, (tert-butylamido)fluorenyl-1,2-ethanediyltitanium dichloride, (tert-butylamido)fluorenyl-1,2-ethanediyltitanium dimethyl, (tert-butylamido)indenyldimethylsilanetitanium dichloride, (tert-butylamido)indenyldimethylsilanetitanium dimethyl, (tert-butylamido) tetrahydroindenyldimethylsilanetitanium dichloride, (tert-butylamido)tetrahydroindenyldimethylsilanetitanium dimethyl, (tert-butylamido) fluorenyldimethylsilanetitanium dichloride, (tert-butylamido)fluorenyldimethylsilanetitanium dimethyl, (dimethylaminomethyl)tetramethylcyclopentadienyltitanium (III) dichloride, (dimethylaminoethyl) tetramethylcyclopentadienyltitanium (III) dichloride, (dimethylaminopropyl)tetramethylcyclopentadienyltitanium (III) dichloride, (N-pyrrolidinylethyl)tetramethylcyclopentadienyltitanium dichloride, (B-dimethylaminoborabenzene) cyclopentadienyltitanium dichloride, cyclopentadienyl(9-mesitylboraanthracenyl)titanium dichloride, 2,2'-thiobis(4-methyl-6-tert-butylphenoxy)titanium dichloride, 2,2'-thiobis[4-methyl-6-(1-methylethyl)phenoxy]titanium dichloride, 2,2'-thiobis[4,6-dimethylphenoxy]titanium dichloride, 2,2'-thiobis(4-methyl-6-tert-butylphenoxy)titanium dichloride, 2,2'-methylenebis(4-methyl-6-tert-butylphenoxy)titanium dichloride, 2,2'-ethylenebis(4-methyl-6-tert-butylphenoxy) titanium dichloride, 2,2'-sulfinylbis(4-methyl-6-tert-butylphenoxy)titanium dichloride, 2,2'-(4,4',6,6'-tetra-tert-butyl-1,1'-biphenoxy)titanium dichloride, 2,2'-thiobis(4-methyl-6-tert-butylphenoxy)titanium diisopropoxide, 2,2'-methylenebis(4-methyl-6-tert-butylphenoxy)titanium diisopropoxide, 2,2'-ethylenebis(4-methyl-6-tert-butylphenoxy)titanium diisopropoxide, 2,2'-sulfinylbis(4-methyl-6-tert-butylphenoxy)titanium diisopropoxide, (di-tert-butyl-1,3-propanediamido)titanium dichloride, (dicyclohexyl-1,3-propanediamido)titanium dichloride, [bis(trimethylsilyl)-1,3-propanediamido]titanium dichloride, [bis(tert-butyldimethylsilyl)-1,3-propanediamido]titanium dichloride, [bis(2,6-dimethylphenyl)-1,3-propanediamido] titanium dichloride, [bis(2,6-diisopropylphenyl)-1,3-propanediamido]titanium dichloride, [bis(2,6-di-tert-butylphenyl)-1,3-propanediamido]titanium dichloride, [bis(triisopropylsilyl)naphthalenediamido]titanium dichloride, [bis(trimethylsilyl)naphthalenediamido]titanium dichloride, [bis(tert-butyldimethylsilyl)naphthalenediamido]titanium dichloride, [bis(tert-butyldimethylsilyl)naphthalenediamido]titanium dibromide, [hydrotris(3,5-dimethylpyrazolyl) borate]titanium trichloride, [hydrotris(3,5-dimethylpyrazolyl)borate]titanium tribromide, [hydrotris(3,5-dimethylpyrazolyl)borate]titanium triiodide, [hydrotris(3,5-diethylpyrazolyl)borate]titanium trichloride, [hydrotris(3,5-diethylpyrazolyl)borate]titanium tribromide, [hydrotris(3,5-diethylpyrazolyl)borate]titanium triiodide, [hydrotris(3,5-di-tert-butylpyrazolyl)borate]titanium trichloride, [hydrotris(3, 5-di-tert-butylpyrazolyl)borate]titanium tribromide, [hydrotris(3,5-di-tert-butylpyrazolyl)borate]titanium triiodide, [tris(3,5-dimethylpyrazolyl)methyl]titanium trichloride, [tris(3,5-dimethylpyrazolyl)methyl]titanium tribromide, [tris(3,5-dimethylpyrazolyl)methyl]titanium triiodide, [tris(3,5-diethylpyrazolyl)methyl]titanium trichloride, [tris(3,5-diethylpyrazolyl)methyl]titanium tribromide, [tris(3,5-diethylpyrazolyl)methyl]titanium triiodide, [tris(3,5-di-tert-butylpyrazolyl)methyl]titanium trichloride, [tris(3,5-di-tert-butylpyrazolyl)methyl]titanium tribromide, and [tris(3,5-di-tert-butylpyrazolyl)methyl]titanium triiodide, [N-(2,6-di(1-methylethyl)phenyl)amido)(o-tolyl)(α-naphthalene-2-diyl (6-pyridine-2-diyl)methane]titanium dichloride, [N-(2,6-di (1-methylethyl)phenyl)amido)(2-isopropylphenyl)(α-naphthalene-2-diyl(6-pyridine-2-diyl)methane]titanium dichloride, [N-(2,6-di(1-methylethyl)phenyl)amido) (phenanthrene-5-yl)(α-naphthalene-2-diyl(6-pyridine-2-diyl)methane)]titanium dichloride; and compounds obtained by changing "titanium" contained in the above compounds to "zirconium" or "hafnium"; compounds obtained by changing "(2-phenoxy)" contained in the above compounds to "(3-phenyl-2-phenoxy)", "(3-trimethylsilyl-2-phenoxy)" or "(3-tert-butyldimethylsilyl-2-phenoxy)"; compounds obtained by changing "dimethylsilylene" contained in the above compounds to "diethylsilylene", "diphenylsilylene" or "dimethoxysilylene"; and compounds obtained by changing "dichloride" contained in the above compounds to "difluoride", "dibromide", "diiodide", "dimethoxide", "diethoxide", "di-n-butoxide", "diisopropoxide", "diphenoxide", "dimethide", or "chloridemethide".

Among transition metal compounds represented by formula [3], examples of the compound whose $M^1$ is a nickel atom, a palladium atom, a cobalt atom, a rhodium atom, or a ruthenium atom are 2,2'-methylenebis[(4R)-4-phenyl-5,5'-dimethyloxazoline]nickel dichloride, 2,2'-methylenebis[(4R)-4-phenyl-5,5'-dimethyloxazoline]nickel dibromide, 2,2'-methylenebis[(4R)-4-phenyl-5,5'-diethyloxazoline] nickel dichloride, 2,2'-methylenebis[(4R)-4-phenyl-5,5'-diethyloxazoline]nickel dibromide, 2,2'-methylenebis[(4R)-4-phenyl-5,5'-di-n-propyloxazoline]nickel dichloride, 2,2'-methylenebis[(4R)-4-phenyl-5,5'-di-n-propyloxazoline] nickel dibromide, 2,2'-methylenebis[(4R)-4-phenyl-5,5'-diisopropyloxazoline]nickel dichloride, 2,2'-methylenebis [(4R)-4-phenyl-5,5'-diisopropyloxazoline]nickel dibromide, 2,2'-methylenebis[(4R)-4-phenyl-5,5'-dicyclohexyloxazoline]nickel dichloride, 2,2'-methylenebis[(4R)-4-phenyl-5,5'-dicyclohexyloxazoline]nickel dibromide, 2,2'-methylenebis[(4R)-4-phenyl-5,5'-dimethoxyoxazoline]nickel dichloride, 2,2'-methylenebis[(4R)-4-phenyl-5,5'-dimethoxyoxazoline]nickel dibromide, 2,2'-methylenebis [(4R)-4-phenyl-5,5'-diethoxyoxazoline]nickel dichloride, 2,2'-methylenebis[(4R)-4-phenyl-5,5'-diethoxyoxazoline] nickel dibromide, 2,2'-methylenebis[(4R)-4-phenyl-5,5'-diphenyloxazoline]nickel dichloride, 2,2'-methylenebis [(4R)-4-phenyl-5,5'-diphenyloxazoline]nickel dibromide, 2,2'-methylenebis[(4R)-4-methyl-5,5-di-(2-methylphenyl) oxazoline]nickel dibromide, 2,2'-methylenebis[(4R)-4-methyl-5,5-di-(3-methylphenyl)oxazoline]nickel dibromide, 2,2'-methylenebis[(4R)-4-methyl-5,5-di-(4-methylphenyl) oxazoline]nickel dibromide, 2,2'-methylenebis[(4R)-4-methyl-5,5-di-(2-methoxyphenyl)oxazoline]nickel dibromide, 2,2'-methylenebis[(4R)-4-methyl-5,5-di-(3-methoxyphenyl) oxazoline]nickel dibromide, 2,2'-methylenebis[(4R)-4-methyl-5,5-di-(4-methoxyphenyl)oxazoline]nickel dibromide, 2,2'-methylenebis[spiro{(4R)-4-methyloxazoline-5,1'-cyclobutane}]nickel dibromide, 2,2'-methylenebis[spiro{(4R)-4-methyloxazoline-5,1'-cyclopentane}]nickel dibromide, 2,2'-methylenebis[spiro{(4R)-4-methyloxazoline-5,1'-cyclohexane}]nickel dibromide, 2,2'-methylenebis[spiro{ (4R)-4-methyloxazoline-5,1'-cycloheptane}]nickel dibromide, 2,2'-methylenebis[(4R)-4-isopropyl-5,5-dimethyloxazoline]nickel dibromide, 2,2'-methylenebis [(4R)-4-isopropyl-5,5-diethyloxazoline]nickel dibromide, 2,2'-methylenebis[(4R)-4-isopropyl-5,5-di-n-propyloxazoline]nickel dibromide, 2,2'-methylenebis[(4R)-4-isopropyl-5,5-diisopropyloxazoline]nickel dibromide, 2,2'-methylenebis[(4R)-4-isopropyl-5,5-dicyclohexyloxazoline]nickel dibromide, 2,2'-methylenebis[(4R)-4-isopropyl-5,5-diphenyloxazoline]nickel dibromide, 2,2'-methylenebis[(4R)-4-isopropyl-5,5-di-(2-methylphenyl)oxazoline]nickel dibromide, 2,2'-methylenebis[(4R)-4-isopropyl-5,5-di-(3-methylphenyl)oxazoline]nickel dibromide, 2,2'-methylenebis[(4R)-4-isopropyl-5,5-di-(4-methylphenyl) oxazoline]nickel dibromide, 2,2'-methylenebis[(4R)-4- isopropyl-5,5-di-(2-methoxyphenyl)oxazoline]nickel dibromide, 2,2'-methylenebis[(4R)-4-isopropyl-5,5-di-(3-methoxyphenyl)oxazoline]nickel dibromide, 2,2'-methylenebis[(4R)-4-isopropyl-5,5-di-(4-methoxyphenyl)oxazoline]nickel dibromide, 2,2'-methylenebis[spiro{(4R)-4-isopropyloxazoline-5,1'-cyclobutane}]nickel dibromide, 2,2'-methylenebis[spiro{(4R)-4-isopropyloxazoline-5,1'-cyclopentane}]nickel dibromide, 2,2'-methylenebis[spiro{(4R)-4-isopropyloxazoline-5,1'-cyclohexane}]nickel dibromide, 2,2'-methylenebis[spiro{(4R)-4-isopropyloxazoline-5,1'-cycloheptane}]nickel dibromide, 2,2'-methylenebis[(4R)-4-isobutyl-5,5-dimethyloxazoline]nickel dibromide, 2,2'-methylenebis[(4R)-4-isobutyl-5,5-diethyloxazoline] nickel dibromide, 2,2'-methylenebis[(4R)-4-isobutyl-5,5-di-n-propyloxazoline]nickel dibromide, 2,2'-methylenebis[(4R)-4-isobutyl-5,5-diisopropyloxazoline]nickel dibromide, 2,2'-methylenebis[(4R)-4-isobutyl-5,5-dicyclohexyloxazoline]nickel dibromide, 2,2'-methylenebis[(4R)-4-isobutyl-5,5-diphenyloxazoline]nickel dibromide, 2,2'-methylenebis[(4R)-4-isobutyl-5,5-di-(2-methylphenyl)oxazoline]nickel dibromide, 2,2'-methylenebis[(4R)-4-isobutyl-5,5-di-(3-methylphenyl)oxazoline]nickel dibromide, 2,2'-methylenebis[(4R)-4-isobutyl-5,5-di-(4-methylphenyl)oxazoline]nickel dibromide, 2,2'-methylenebis[(4R)-4-isobutyl-5,5-di-(2-methoxyphenyl)oxazoline]nickel dibromide, 2,2'-methylenebis[(4R)-4-isobutyl-5,5-di-(3-methoxyphenyl)oxazoline]nickel dibromide, 2,2'-methylenebis[(4R)-4-isobutyl-5,5-di-(4-methoxyphenyl)oxazoline]nickel dibromide, 2,2'-methylenebis[spiro{(4R)-4-isobutyloxazoline-5,1'-cyclobutane}]nickel dibromide, 2,2'-methylenebis[spiro{(4R)-4-isobutyloxazoline-5,1'-cyclopentane}]nickel dibromide, 2,2'-methylenebis[spiro{(4R)-4-isobutyloxazoline-5,1'-cyclohexane}]nickel dibromide, 2,2'-methylenebis[spiro{(4R)-4-isobutyloxazoline-5,1'-cycloheptane}]nickel dibromide, 2,2'-methylenebis[(4R)-4-tert-butyl-5,5-dimethyloxazoline]nickel dibromide, 2,2'-methylenebis[(4R)-4-tert-butyl-5,5-diethyloxazoline] nickel dibromide, 2,2'-methylenebis[(4R)-4-tert-butyl-5,5-di-n-propyloxazoline]nickel dibromide, 2,2'-methylenebis[(4R)-4-tert-butyl-5,5-diisopropyloxazoline]nickel dibromide, 2,2'-methylenebis[(4R)-4-tert-butyl-5,5-dicyclohexyloxazoline]nickel dibromide, 2,2'-methylenebis[(4R)-4-tert-butyl-5,5-diphenyloxazoline]nickel dibromide, 2,2'-methylenebis[(4R)-4-tert-butyl-5,5-dicyclohexyloxazoline] nickel dibromide, 2,2'-methylenebis[(4R)-4-tert-butyl-5,5-diphenyloxazoline]nickel dibromide, 2,2'-methylenebis[(4R)-4-tert-butyl-5,5-di-(2-methylphenyl)oxazoline]nickel dibromide, 2,2'-methylenebis[(4R)-4-tert-butyl-5,5-di-(3-methylphenyl)oxazoline]nickel dibromide, 2,2'-methylenebis[(4R)-4-tert-butyl-5,5-di-(4-methylphenyl)oxazoline] nickel dibromide, 2,2'-methylenebis[(4R)-4-tert-butyl-5,5-di-(2-methoxyphenyl)oxazoline]nickel dibromide, 2,2'-methylenebis[(4R)-4-tert-butyl-5,5-di-(3-methoxyphenyl)oxazoline]nickel dibromide, 2,2'-methylenebis[(4R)-4-tert-butyl-5,5-di-(4-methoxyphenyl)oxazoline]nickel dibromide, 2,2'-methylenebis[spiro{(4R)-4-tert-butyloxazoline-5,1'-cyclobutane}]nickel dibromide, 2,2'-methylenebis[spiro{(4R)-4-tert-butyloxazoline-5,1'-cyclopentane}]nickel dibromide, 2,2'-methylenebis[spiro{(4R)-4-tert-butyloxazoline-5,1'-cyclohexane}]nickel dibromide, 2,2'-methylenebis[spiro{(4R)-4-tert-butyloxazoline-5,1'-cycloheptane}]nickel dibromide, 2,2'-methylenebis[(4R)-4-phenyl-5,5-dimethyloxazoline]nickel dibromide, 2,2'-methylenebis[(4R)-4-phenyl-5,5-diethyloxazoline]nickel dibromide, 2,2'-methylenebis[(4R)-4-phenyl-5,5-di-n-propyloxazoline]nickel dibromide, 2,2'-methylenebis[(4R)-4-phenyl-5,5-diisopropyloxazoline]nickel dibromide, 2,2'-methylenebis[(4R)-4-phenyl-5,5-dicyclohexyloxazoline]nickel dibromide, 2,2'-methylenebis[(4R)-4-phenyl-5,5-diphenyloxazoline]nickel dibromide, 2,2'-methylenebis[(4R)-4-phenyl-5,5-di-(2-methylphenyl)oxazoline]nickel dibromide, 2,2'-methylenebis[(4R)-4-phenyl-5,5-di-(3-methylphenyl)oxazoline]nickel dibromide, 2,2'-methylenebis[(4R)-4-phenyl-5,5-di-(4-methylphenyl)oxazoline]nickel dibromide, 2,2'-methylenebis[(4R)-4-phenyl-5,5-di-(2-methoxyphenyl)oxazoline]nickel dibromide, 2,2'-methylenebis[(4R)-4-phenyl-5,5-di-(3-methoxyphenyl)oxazoline]nickel dibromide, 2,2'-methylenebis[(4R)-4-phenyl-5,5-di-(4-methoxyphenyl)oxazoline]nickel dibromide, 2,2'-methylenebis[spiro{(4R)-4-phenyloxazoline-5,1'-cyclobutane}]nickel dibromide, 2,2'-methylenebis[spiro{(4R)-4-phenyloxazoline-5,1'-cyclopentane}]nickel dibromide, 2,2'-methylenebis[spiro{(4R)-4-phenyloxazoline-5,1'-cyclohexane}]nickel dibromide, 2,2'-methylenebis[spiro{(4R)-4-phenyloxazoline-5,1'-cycloheptane}]nickel dibromide, 2,2'-methylenebis[(4R)-4-benzyl-5,5-dimethyloxazoline]nickel dibromide, 2,2'-methylenebis[(4R)-4-benzyl-5,5-diethyloxazoline] nickel dibromide, 2,2'-methylenebis[(4R)-4-benzyl-5,5-di-n-propyloxazoline]nickel dibromide, 2,2'-methylenebis[(4R)-4-benzyl-5,5-diisopropyloxazoline]nickel dibromide, 2,2'-methylenebis[(4R)-4-benzyl-5,5-dicyclohexyloxazoline]nickel dibromide, 2,2'-methylenebis[(4R)-4-benzyl-5,5-diphenyloxazoline]nickel dibromide, 2,2'-methylenebis[(4R)-4-benzyl-5,5-di-(2-methylphenyl)oxazoline]nickel dibromide, 2,2'-methylenebis[(4R)-4-benzyl-5,5-di-(3-methylphenyl)oxazoline]nickel dibromide, 2,2'-methylenebis[(4R)-4-benzyl-5,5-di-(4-methylphenyl)oxazoline]nickel dibromide, 2,2'-methylenebis[(4R)-4-benzyl-5,5-di-(2-methoxyphenyl)oxazoline]nickel dibromide, 2,2'-methylenebis[(4R)-4-benzyl-5,5-di-(3-methoxyphenyl)oxazoline] nickel dibromide, 2,2'-methylenebis[(4R)-4-benzyl-5,5-di-(4-methoxyphenyl)oxazoline]nickel dibromide, 2,2'-methylenebis[spiro{(4R)-4-benzyloxazoline-5,1'-cyclobutane}]nickel dibromide, 2,2'-methylenebis[spiro{(4R)-4-benzyloxazoline-5,1'-cyclopentane}]nickel dibromide, 2,2'-methylenebis[spiro{(4R)-4-benzyloxazoline-5,1'-cyclohexane}]nickel dibromide, and 2,2'-methylenebis[spiro{(4R)-4-benzyloxazoline-5,1'-cycloheptane}] nickel dibromide; and antipodes of the above respective compounds; compounds obtained by reversing a steric configuration of an asymmetric carbon atom on one oxazoline ring contained in the above bisoxazoline compounds; and compounds obtained by changing "dibromide" contained in the above compounds to "dichloride", "dimethoxide" or "dimethide".

Among transition metal compounds represented by formula [3], further examples of the compound whose $M^1$ is a nickel atom are [hydrotris(3,5-dimethylpyrazolyl)borate]nickel chloride, [hydrotris(3,5-dimethylpyrazolyl)borate]nickel bromide, [hydrotris(3,5-dimethylpyrazolyl)borate]nickel iodide, [hydrotris(3,5-diethylpyrazolyl)borate]nickel chloride, [hydrotris(3,5-diethylpyrazolyl)borate]nickel bromide, [hydrotris(3,5-diethylpyrazolyl)borate]nickel iodide, [hydrotris(3,5-di-tert-butylpyrazolyl)borate]nickel chloride, [hydrotris(3,5-di-tert-butylpyrazolyl)borate]nickel bromide, and [hydrotris(3,5-di-tert-butylpyrazolyl)borate]nickel iodide; and nickel compounds represented by following formula [7]:

[7]

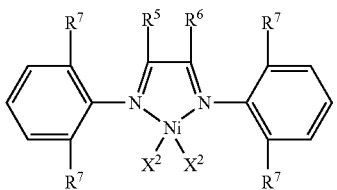

wherein X² is a fluorine atom, a chlorine atom, an iodine atom, a methyl group, an ethyl group, a n-propyl group, an isopropyl group, a n-butyl group, a phenyl group, a benzyl group, or a trimethylsilylmethyl group; R⁵ and R⁶ are a hydrogen atom, a methyl group, or a naphthalene-1,8-dily group formed by a mutual linking thereof; and R⁷ is a methyl group.

Above X², R⁵, R⁶ and R⁷ have following three combinations (1) to (3), each of which has eleven combinations depending on X², and therefore the total number of their combination is 33:

(1) a combination, wherein R⁵ and R⁶ are a hydrogen atom, R⁷ is a methyl group, and X² is a fluorine atom, a chlorine atom, an iodine atom, a methyl group, an ethyl group, a n-propyl group, an isopropyl group, a n-butyl group, a phenyl group, a benzyl group, or a trimethylsilylmethyl group;

(2) a combination, wherein R⁵ and R⁶ are a methyl group, and R⁷ and X² are the same as the above;

(3) a combination, wherein R⁵ and R⁶ are a naphthalene-1, 8-dily group, and R⁷ and X² are the same as the above.

Still further examples of the transition metal compound in the present invention are compounds obtained by changing "nickel" contained in the above nickel compounds to "palladium", "cobalt", "rhodium" or "ruthenium".

Among transition metal compounds represented by formula [3], further examples of the compound whose M¹ is an iron atom, a cobalt atom or a nickel atom are 2,6-bis-[1-(2,6-dimethylphenylimino)ethyl]pyridineiron dichloride, 2,6-bis-[1-(2,6-diisopropylphenylimino)ethyl]pyridineiron dichloride, 2,6-bis-[1-(2-tert-butyl-phenylimino)ethyl]pyridineiron dichloride, [hydrotris(3,5-dimethylpyrazolyl)borate]iron chloride, [hydrotris(3,5-dimethylpyrazolyl)borate]iron bromide, [hydrotris(3,5-dimethylpyrazolyl)borate]iron iodide, [hydrotris(3,5-diethylpyrazolyl)borate]iron chloride, [hydrotris(3,5-diethylpyrazolyl)borate]iron bromide, [hydrotris(3,5-diethylpyrazolyl)borate]iron iodide, [hydrotris(3,5-di-tert-butylpyrazolyl)borate]iron chloride, [hydrotris(3,5-di-tert-butylpyrazolyl)borate]iron bromide, and [hydrotris(3,5-di-tert-butylpyrazolyl)borate]iron iodide; and compounds obtained by changing "iron" contained in the above compounds to "cobalt" or "nickel".

Examples of the p-oxo type transition metal compound of the transition metal compound represented by formula [3] are
μ-oxobis[isopropylidene(cyclopentadienyl)(2-phenoxy)titanium chloride],
μ-oxobis[isopropylidene(cyclopentadienyl)(2-phenoxy)titanium methoxide],
μ-oxobis[isopropylidene(cyclopentadienyl)(3-tert-butyl-5-methyl-2-phenoxy)titanium chloride],
μ-oxobis[isopropylidene(cyclopentadienyl)(3-tert-butyl-5-methyl-2-phenoxy)titanium methoxide],
μ-oxobis[isopropylidene(methylcyclopentadienyl)(2-phenoxy)titanium chloride],
μ-oxobis[isopropylidene(methylcyclopentadienyl)(2-phenoxy)titanium methoxide],
μ-oxobis[isopropylidene(methylcyclopentadienyl)(3-tert-butyl-5-methyl-2-phenoxy)titanium chloride],
μ-oxobis[isopropylidene(methylcyclopentadienyl) (3-tert-butyl-5-methyl-2-phenoxy)titanium methoxide],
μ-oxobis[isopropylidene(tetramethylcyclopentadienyl)(2-phenoxy)titanium chloride],
μ-oxobis[isopropylidene(tetramethylcyclopentadienyl)(2-phenoxy)titanium methoxide],
μ-oxobis[isopropylidene(tetramethylcyclopentadienyl)(3-tert-butyl-5-methyl-2-phenoxy)titanium chloride],
μ-oxobis[isopropylidene(tetramethylcyclopentadienyl)(3-tert-butyl-5-methyl-2-phenoxy)titanium methoxide],
μ-oxobis[dimethylsilylene(cyclopentadienyl)(2-phenoxy)titanium chloride],
μ-oxobis[dimethylsilylene(cyclopentadienyl)(2-phenoxy)titanium methoxide],
μ-oxobis[dimethylsilylene(cyclopentadienyl)(3-tert-butyl-5-methyl-2-phenoxy)titanium chloride],
μ-oxobis[dimethylsilylene(cyclopentadienyl)(3-tert-butyl-5-methyl-2-phenoxy)titanium methoxide],
μ-oxobis[dimethylsilylene(methylcyclopentadienyl)(2-henoxy)titanium chloride],
μ-oxobis[dimethylsilylene(methylcyclopentadienyl)(2-henoxy)titanium methoxide],
μ-oxobis[dimethylsilylene(methylcyclopentadienyl)(3-tert-butyl-5-methyl-2-phenoxy)titanium chloride],
μ-oxobis[dimethylsilylene(methylcyclopentadienyl)(3-tert-butyl-5-methyl-2-phenoxy)titanium methoxide],
μ-oxobis[dimethylsilylene(tetramethylcyclopentadienyl)(2-phenoxy)titanium chloride],
μ-oxobis[dimethylsilylene(tetramethylcyclopentadienyl)(2-phenoxy)titanium methoxide],
μ-oxobis[dimethylsilylene(tetramethylcyclopentadienyl)(3-tert-butyl-5-methyl-2-phenoxy)titanium chloride],
μ-oxobis[dimethylsilylene(tetramethylcyclopentadienyl)(3-tert-butyl-5-methyl-2-phenoxy)titanium methoxide],
di-μ-oxobis[isopropylidene(cyclopentadienyl)(2-phenoxy) titanium],
di-μ-oxobis[isopropylidene(cyclopentadienyl)(3-tert-butyl-5-methyl-2-phenoxy)titanium],
di-μ-oxobis[isopropylidene(methylcyclopentadienyl)(2-phenoxy)titanium],
di-μ-oxobis[isopropylidene(methylcyclopentadienyl)(3-tert-butyl-5-methyl-2-phenoxy)titanium],
di-μ-oxobis[isopropylidene(tetramethylcyclopentadienyl) (2-phenoxy)titanium],
di-μ-oxobis[isopropylidene(tetramethylcyclopentadienyl) (3-tert-butyl-5-methyl-2-phenoxy)titanium],
di-μ-oxobis[dimethylsilylene(cyclopentadienyl)(2-phenoxy)titanium],
di-μ-oxobis[dimethylsilylene(cyclopentadienyl)(3-tert-butyl-5-methyl-2-phenoxy)titanium],
di-μ-oxobis[dimethylsilylene(methylcyclopentadienyl)(2-phenoxy)titanium],
di-μ-oxobis[dimethylsilylene(methylcyclopentadienyl)(3-tert-butyl-5-methyl-2-phenoxy)titanium],
di-μ-oxobis[dimethylsilylene(tetramethylcyclopentadienyl) (2-phenoxy)titanium], and
di-μ-oxobis[dimethylsilylene(tetramethylcyclopentadienyl) (3-tert-butyl-5-methyl-2-phenoxy)titanium].

The above transition metal compounds may be used in combination of two or more thereof. The transition metal compound in the present invention is preferably a transition metal compound represented by formula [3] whose M¹ is a transition metal atom of group 4, a nickel atom or a palladium atom; more preferably a transition metal compound represented thereby whose M¹ is a transition metal atom of group 4; and further preferably a transition metal compound represented thereby whose $M^1$ is a transition metal atom of group 4, and whose one or more $L^1$s are a cyclopentadiene-containing anionic group.

Among the above-mentioned further preferable transition metal compound, whose $M^1$ is a transition metal atom of group 4, and whose one or more $L^1$s are a cyclopentadiene-containing anionic group, preferred is a transition metal compound represented by following formula [8] or [9], and more preferred is a transition metal compound represented by formula [9]:

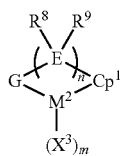
[8]

wherein $M^2$ is a transition metal atom of group 4 of the periodic table; $Cp^1$ is a cyclopentadiene-containing anionic group having 5 to 30 carbon atoms; $R^8$ and $R^9$ are a hydrogen atom or a hydrocarbyl group having 1 to 20 carbon atoms, and they are different from each other; E is an atom of group 14 of the periodic table; $X^3$ is a halogen atom, a hydrocarbyl group having 1 to 20 carbon atoms, or a hydrocarbyloxy group having 1 to 20 carbon atoms; G is a cyclopentadiene-containing anionic group having 5 to 30 carbon atoms, or a group represented by following formula [10]; n is an integer of 1 to 6; m is 1 or 2; when n is 2 or more, plural Es, $R^8$s and $R^9$s are the same as, or different from one another; and when m is 2, two $X^3$s are the same as, or different from each other;

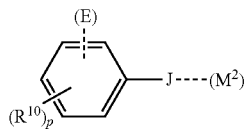
[10]

wherein J is an atom of group 16 of the periodic table; $R^{10}$ is a hydrocarbyl group having 1 to 20 carbon atoms; the dashed line - - - ($M^2$) is a bond to $M^2$ in formula [8]; the dashed line - - - (E) is a bond to E in formula [8]; and p is an integer of 0 to 4, and when p is 2 or more, plural $R^{10}$s are the same as, or different from one another;

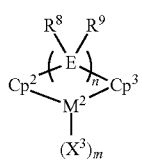
[9]

wherein $M^2$ is a transition metal atom of group 4 of the periodic table; $Cp^1$ and $Cp^3$ are a cyclopentadiene-containing anionic group having 5 to 30 carbon atoms, and they are different from each other; $R^8$ and $R^9$ are a hydrogen atom or a hydrocarbyl group having 1 to 20 carbon atoms, and they are different from each other; E is an atom of group 14 of the periodic table; $X^3$ is a halogen atom, a hydrocarbyl group having 1 to 20 carbon atoms, or a hydrocarbyloxy group having 1 to 20 carbon atoms; n is an integer of 1 to 6; m is 1 or 2; when n is 2 or more, plural Es, $R^8$s and $R^9$s are the same as, or different from one another; and when m is 2, two $X^3$s are the same as, or different from each other.

Examples of $M^2$ in formulas [8] and [9] are a titanium atom, a zirconium atom and a hafnium atom. Among them, preferred is a zirconium atom. Examples of E therein are a carbon atom and a silicon atom. Examples of the cyclopentadiene-containing anionic group having 5 to 30 carbon atoms of G, $Cp^1$, $Cp^2$ and $Cp^3$ in formula [8] or [9] are the same as those above-exemplified as $L^1$ in formula [3]. Examples of the halogen atom, the hydrocarbyl group having 1 to 20 carbon atoms and the hydrocarbyloxy group having 1 to 20 carbon atoms of $X^3$ in formulas [8] and [9] are the same as those above-exemplified as $X^1$ in formula [3], respectively.

Examples of the hydrocarbyl group having 1 to 20 carbon atoms of $R^8$ and $R^9$ in formulas [8] and [9] are an alkyl group having 1 to 20 carbon atoms, an alkenyl group giving 2 to 20 carbon atoms, an aryl group having 6 to 20 carbon atoms, and an aralkyl group having 7 to 20 carbon atoms. The hydrocarbyl group having 1 to 20 carbon atoms of $R^8$ and $R^9$ may have a substituent. An example the substituent is a hydrocarbyloxy group such as an alkoxy group (for example, a methoxy group and an ethoxy group), an aryloxy group (for example, a phenoxy group), and an aralkyloxy group (for example, a benzyloxy group).

Examples of the alkyl group having 1 to 20 carbon atoms of $R^8$ and $R^9$ are a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-heptyl group, a n-octyl group, a n-decyl group, a n-dodecyl group, a n-pentadecyl group and a n-eicosyl group. Among them, preferred is a methyl group, an ethyl group, an isopropyl group, a tert-butyl group, an isobutyl group.

Examples of the alkenyl group having 2 to 20 carbon atoms of $R^8$ and $R^9$ are a vinyl group, an allyl group, a propenyl group, a 2-methyl-2-propenyl group, a homoallyl group, a pentenyl group, a hexenyl group, a heptenyl group, an octenyl group, a nonenyl group, and a decenyl group.

Examples of the aryl group having 6 to 20 carbon atoms of $R^8$ and $R^9$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, preferred is a phenyl group.

Examples of the aralkyl group having 7 to 20 carbon atoms of $R^8$ and $R^9$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-trimethylphenyl)

methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl) methyl group, a (tert-butylphenyl)methyl group, an (isobutylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a naphthylmethyl group, and an anthracenylmethyl group. Among them, preferred is a benzyl group.

$R^8$ and $R^9$ in above formulas [8] and [9] are preferably an alkyl group having 1 to 20 carbon atoms, or an aryl group having 6 to 20 carbon atoms, more preferably an alkyl group having 1 to 20 carbon atoms, further preferably a methyl group, an ethyl group, a n-propyl group, an isopropyl group, a n-butyl group, a sec-butyl group, a tert-butyl group, or an isobutyl group, and particularly preferably an ethyl group.

Examples of J in above formula [10] are an oxygen atom and a sulfur atom. Among them, preferred is an oxygen atom. Examples of the hydrocarbyl group having 1 to 20 carbon atoms of $R^{10}$ in formula [10] are the same as those above-exemplified as the hydrocarbyl group of $R^8$ and $R^9$ in formulas [8] and [9].

The transition metal compound in the present invention is preferably the transition metal compound represented by formula [3] whose $M^1$ is a transition metal atom of group 4, a nickel atom or a palladium atom, and one or more of whose $X^1$ are a hydrocarbyl group having 1 to 20 carbon atoms, more preferably the transition metal compound represented thereby whose $M^1$ is a transition metal atom of group 4, and one or more of whose $X^1$ are a hydrocarbyl group having 1 to 20 carbon atoms, and further preferably the transition metal compound represented thereby whose $M^1$ is a transition metal atom of group 4, one or more of whose $X^1$ are a hydrocarbyl group having 1 to 20 carbon atoms, and one or more of whose $L^1$ are a cyclopentadiene-containing anionic group. Among the above further preferable transition metal compound, preferred is the transition metal compound represented by formula [8], and more is the transition metal compound represented by formula [9].

An organoaluminum compound in the present invention may be a compound known in the art, and is preferably an organoaluminum compound represented by following formula [11]:

$$(R^{11})_d Al(X^4)_{3-d} \quad [11]$$

wherein $R^{11}$ is a hydrocarbyl group having 1 to 24 carbon atoms; $X^4$ is a hydrogen atom, a halogen atom, or a hydrocarbyloxy group having 1 to 24 carbon atoms; and d is an integer of 1 to 3, and when d is 2 or 3, plural $R^{11}$s are the same as, or different from one another, and when d is 1, two $X^4$s are the same as, or different from each other.

$R^{11}$ is preferably an alkyl group such as a methyl group, an ethyl group, a n-propyl group, a n-butyl group, an isobutyl group, a n-hexyl group, a 2-methylhexyl group, and a n-octyl group. Among them, preferred is an ethyl group, a n-butyl group, an isobutyl group, a n-hexyl group, or a n-octyl group.

Examples of the halogen atom of $X^4$ are a fluorine atom, a chlorine atom, a bromine atom, and an iodine atom. Among them, preferred is a chlorine atom.

Examples of the hydrocarbyloxy group having 1 to 24 carbon atoms of $X^4$ are an alkoxy group having 1 to 24 carbon atoms, an aryloxy group having 6 to 24 carbon atoms, and an aralkyloxy group having 7 to 24 carbon atoms.

Examples of the above alkoxy group are a methoxy group, an ethoxy group, a n-propoxy group, an isopropoxy group, a n-butoxy group, a sec-butoxy group, a tert-butoxy group, a n-pentoxy group, and a n-eicosoxy group. Among them, preferred is a methoxy group, an ethoxy group or a tert-butoxy group.

Examples of the above aryloxy group are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, and an anthrathenoxy group.

Examples of the above aralkyloxy group are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl) methoxy group, a (2,5-dimethylphenyl)methoxy group, a (2,6-dimethylphenyl)methoxy group, a (3,4-dimethylphenyl) methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl) methoxy group, a (2,3,4,5-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl) methoxy group, a (n-decylphenyl)methoxy group, a (n-tetradecylphenyl)methoxy group, a naphthylmethoxy group, and an anthrathenylmethoxy group. Among them, preferred is a benzyloxy group.

Examples of the organoaluminum compound represented by formula [11] are a trialkylaluminum such as trimethylaluminum, triethylaluminum, tri-n-propylaluminum, tri-n-butylaluminum, triisobutylaluminum, tri-n-hexylaluminum, and tri-n-octylaluminum; a dialkylaluminum chloride such as dimethylaluminum chloride, diethylaluminum chloride, di-n-propylaluminum chloride, di-n-butylaluminum chloride, diisobutylaluminum chloride, and di-n-hexylaluminum chloride; an alkylaluminum dichloride such as methylaluminum dichloride, ethylaluminum dichloride, n-propylaluminum dichloride, n-butylaluminum dichloride, isobutylaluminum dichloride, and n-hexylaluminum dichloride; a dialkylaluminum hydride such as dimethylaluminum hydride, diethylaluminum hydride, di-n-propylaluminum hydride, di-n-butylaluminum hydride, diisobutylaluminum hydride, and di-n-hexylaluminum hydride; an alkyl(dialkoxy)aluminum such as methyl(dimethoxy)aluminum, methyl(diethoxy)aluminum, and methyl(di-tert-butoxy)aluminum; a dialkyl(alkoxy) aluminum such as dimethyl(methoxy)aluminum, dimethyl (ethoxy)aluminum, and dimethyl(tert-butoxy)aluminum; an alkyl(diaryloxy)aluminum such as methyl(diphenoxy)aluminum, methylbis(2,6-diisopropylphenoxy)aluminum, and methylbis(2,6-diphenylphenoxy)aluminum; and a dialkyl (aryloxy)aluminum such as dimethyl(phenoxy)aluminum, dimethyl(2,6-diisopropylphenoxy)aluminum, and dimethyl (2,6-diphenylphenoxy)aluminum; and a combination of two or more thereof. The organoaluminum compound is preferably trialkylaluminums. Among them, preferred is trimethylaluminum, triethylaluminum, tri-n-butylaluminum, triisobutylaluminum, tri-n-hexylaluminum, or tri-n-octylaluminum, and more preferred is triisobutylaluminum or tri-n-octylaluminum.

The above-mentioned polymerization catalyst production process-1 uses the catalyst component for addition polymerization in an amount of usually 1 to 1,000,000 mol, preferably 10 to 500,000 mol, and more preferably 20 to 100,000 mol of a metal atom contained in the catalyst component for addition polymerization, per one mol of the transition metal compound.

Above-mentioned polymerization catalyst production process-2 uses the catalyst component for addition polymerization in an amount of usually 1 to 1,000,000 mol, preferably 10 to 500,000 mol, and more preferably 100 to 100,000 mol of a metal atom contained in the catalyst component for addition polymerization, per one mol of the transition metal compound.

Polymerization catalyst production process-2 uses the organoaluminum compound in an amount of preferably 0.01 to 10,000,000 mol, more preferably 0.1 to 1,000,000 mol, further preferably 1 to 100,000 mol, and particularly preferably 10 to 10,000 mol of an aluminum atom contained in the organoaluminum compound, per one mol of a transition metal atom contained in the transition metal compound.

Examples of a method for contacting the catalyst component for addition polymerization with the transition metal compound in polymerization catalyst production process-1 are (1-1) a method comprising contacting those two catalyst components with each other in a catalyst-forming reactor, and supplying the resultant contact product to a polymerization reactor, and (1-2) a method comprising contacting those catalyst components with each other in a polymerization reactor. Those catalyst components are supplied to a catalyst-forming reactor or a polymerization reactor, generally in their solid state or in their solution, suspension or slurry state using a hydrocarbon solvent sufficiently free from materials deactivating those catalyst components, such as water and oxygen. When using a hydrocarbon solvent, a concentration of the catalyst component for addition polymerization is usually 0.001 to 100 mol/liter, and preferably 0.01 to 10 mol/liter from a viewpoint of a molar amount of a metal atom contained in the catalyst component for addition polymerization; and a concentration of the transition metal compound is usually 0.00001 to 1 mol/liter, and preferably 0.0001 to 0.1 mol/liter.

Examples of a method for contacting the catalyst component for addition polymerization, the transition metal compound and the organoaluminum compound with one another in polymerization catalyst production process-2 are (2-1) a method comprising contacting those three catalyst components with one another in a catalyst-forming reactor, and supplying the resultant contact product to a polymerization reactor, (2-2) a method comprising contacting those three catalyst components with one another in a polymerization reactor, and (2-3) a method comprising steps of (i) contacting any two of those three catalyst components with each other in a catalyst-forming reactor, and (ii) supplying the resultant contact product and the remaining catalyst component to a polymerization reactor, thereby contacting them in the polymerization reactor.

More specific examples of above method (2-1) are following methods (2-1-1) to (2-1-4), and preferred is method (2-1-4), wherein the "catalyst component for addition polymerization", "transition metal compound" and "organoaluminum compound" are referred to hereinafter as "component (A)", "component (B)" and "component (C)", respectively:

(2-1-1) a method comprising supplying components (A), (B) and (C) at the same time to a catalyst-forming reactor;

(2-1-2) a method comprising steps of (i) contacting components (A) and (B) with each other in a catalyst-forming reactor, and then (ii) supplying component (C) to the catalyst-forming reactor;

(2-1-3) a method comprising steps of (i) contacting components (A) and (C) with each other in a catalyst-forming reactor, and then (ii) supplying component (B) thereto; and (2-1-4) a method comprising steps of (i) contacting components (B) and (C) with each other in a catalyst-forming reactor, and then (ii) supplying component (A) thereto.

More specific examples of above method (2-2) are following methods (2-2-1) to (2-2-4), and preferred is method (2-2-4):

(2-2-1) a method comprising supplying components (A), (B) and (C) at the same time to a polymerization reactor in the presence of an addition-polymerizable monomer;

(2-2-2) a method comprising steps of (i) contacting components (A) and (B) with each other in a polymerization reactor in the presence of an addition-polymerizable monomer, and then (ii) supplying component (C) to the polymerization reactor in the presence thereof;

(2-2-3) a method comprising steps of (i) contacting components (A) and (C) with each other in a polymerization reactor in the presence of an addition-polymerizable monomer, and then (ii) supplying component (B) to the polymerization reactor in the presence thereof; and (2-2-4) a method comprising steps of (i) contacting components (B) and (C) with each other in a polymerization reactor in the presence of an addition-polymerizable monomer, and then (ii) supplying component (A) to the polymerization reactor in the presence thereof.

More specific examples of above method (2-3) are following methods (2-3-1) to (2-3-3), and preferred is method (2-3-3):

(2-3-1) a method comprising steps of (i) contacting components (A) and (B) with each other in a catalyst-forming reactor, thereby forming a contact product, and then (ii) supplying separately the contact product and component (C) to a polymerization reactor in the presence of an addition-polymerizable monomer;

(2-3-2) a method comprising steps of (i) contacting components (A) and (C) with each other in a catalyst-forming reactor, thereby forming a contact product, and then (ii) supplying separately the contact product and component (B) to a polymerization reactor in the presence of an addition-polymerizable monomer; and (2-3-3) a method comprising steps of (i) contacting components (B) and (C) with each other in a catalyst-forming reactor, thereby forming a contact product, and then (ii) supplying separately the contact product and component (A) to a polymerization reactor in the presence of an addition-polymerizable monomer.

Catalyst components used in polymerization catalyst production process-2 are supplied to a catalyst-forming reactor or a polymerization reactor, generally in their solid state or in their solution, suspension or slurry state using a hydrocarbon solvent sufficiently free from materials deactivating those catalyst components, such as water and oxygen. When using a hydrocarbon solvent, a concentration of the catalyst component for addition polymerization is usually 0.001 to 100 mol/liter, and preferably 0.01 to 10 mol/liter from a viewpoint of a molar amount of a metal atom contained in the catalyst component for addition polymerization; a concentration of the transition metal compound is usually 0.00001 to 1 mol/liter, and preferably 0.0001 to 0.1 mol/liter; and a concentration of the organoaluminum compound is usually 0.0001 to 100 mol/liter, and preferably 0.01 to 10 mol/liter from a viewpoint of a molar amount of an aluminum atom contained in the organoaluminum compound.

Examples of a polymerization method in the process for producing an addition polymer of the present invention are a gas phase polymerization method carried out in a gaseous monomer, and a solution or slurry polymerization method using a solvent. Examples of the solvent are an aliphatic hydrocarbon solvent such as butane, pentane, hexane, heptane and octane; an aromatic hydrocarbon solvent such as benzene and toluene; and a halogenated hydrocarbon solvent such as methylene chloride. Also, the solvent may be an addition-polymerizable monomer such as an olefin, which embodiment is referred to as bulk polymerization in the art.

The polymerization in the present invention is carried out usually for 1 minute to 20 hours, which depends on a type of a target addition polymer and a polymerization reactor, and is carried out in a batch-wise manner, a continuous manner, or a combined manner thereof, in one or more steps having different polymerization conditions from one another.

The above slurry polymerization method is not particularly limited in its polymerization embodiments and polymerization conditions, which embodiments and conditions may be known in the art. The slurry polymerization method is preferably carried out using a continuous polymerization reactor, wherein necessary starting materials such an addition-polymerizable monomer, a comonomer, a diluent (for example, an inert diluent (medium) such as paraffin, cycloparaffin and an aromatic hydrocarbon) and other materials are added, if necessary continuously, to the continuous polymerization reactor, and a produced addition polymer is taken out continuously or periodically from the continuous polymerization reactor. Examples of the polymerization reactor are a loop reactor, and a reactor combining stirrer-equipped plural reactors in series or in parallel, wherein the plural reactors are different from one another in their structure and polymerization reaction condition. The polymerization reactor or its reaction zone has polymerization temperature of usually 0 to about 150° C., and preferably 30 to 100° C., and has polymerization pressure of 0.1 to about 10 MPa, and preferably 0.5 to 5 MPa. The polymerization pressure may be such that a polymerization catalyst is maintained in its suspension state, and a medium and at least part of an addition-polymerizable monomer or comonomer are maintained in their liquid state. The medium, polymerization temperature and pressure may be selected such that a particulate addition polymer is produced, and is recovered in its particulate shape. Molecular weight of the addition polymer can be controlled by a method known in the art, such as a temperature regulation of a reaction zone, and an introduction of hydrogen into the reaction zone. The above-mentioned polymerization catalyst components, an addition-polymerizable monomer and an optionally-used comonomer can be supplied to a polymerization reactor or a reaction zone, in any order, by any method known in the art. For example, they are supplied thereto at the same time or successively.

The above gas phase polymerization method is not particularly limited in its polymerization embodiments and polymerization conditions, which embodiments and conditions may be known in the art. An example of a gas phase polymerization reactor is a fluidized bed reactor, and preferably a fluidized bed reactor having an enlarged part. The reactor may have an internal stirrer. Examples of a method for supplying the above-mentioned polymerization catalyst components to a gas phase polymerization reactor are (1) a method of supplying them in the absence of water or moisture by use of an inert gas (for example, nitrogen and argon), hydrogen or ethylene, and (2) a method of supplying them in their solution or slurry state using a solvent. Those polymerization catalyst components may be supplied to a gas phase polymerization reactor individually, or may be supplied after mutually pre-contacting them in any order. The above gas phase polymerization is carried out at preferably 0 to 300° C., further preferably 10 to 200° C., and particularly preferably 30 to 100° C. In order to control melt-flowability of a produced addition polymer, a molecular weight regulator such as hydrogen may be used. Also, a mixed gas in a gas phase polymerization reactor may contain an inert gas.

The above-mentioned addition polymerization catalyst is used directly (namely, without modification) for producing an addition polymer in the present invention, which polymerization is usually referred to as "main polymerization" in the art. However, the above-mentioned addition polymerization catalyst may be modified by the following method to produce a pre-polymerized catalyst, which can be also used for the main polymerization. The pre-polymerized catalyst can be obtained by polymerizing a small amount of an olefin in the presence of the above-mentioned addition polymerization catalyst, under pre-polymerization conditions known in the art, and such polymerization of a small amount of an olefin is referred to as "pre-polymerization" in contrast to the above main polymerization. The term "addition polymerization catalyst" in the present invention means not only the above-mentioned "addition polymerization catalyst without modification", but also the above-mentioned "pre-polymerized catalyst".

Examples of the addition-polymerizable monomer in the present invention are ethylene; an α-olefin having 3 to 20 carbon atoms such as propylene, 1-butene, 1-pentene, 4-methyl-1-pentene, 5-methyl-1-hexene, 1-hexene, 1-heptene, 1-octene, 1-nonene, and 1-decene; a diolefin such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene, 1,3-butadiene, isoprene, 1,3-hexadinene, 1,3-octadiene, 1,3-cyclooctadiene, and 1,3-cyclohexadiene; a cyclic olefin such as norbornene, 5-methylnorbornene, 5-ethylnorbornene, 5-butylnorbornene, 5-phenylnorbornene, 5-benzylnorbornene, tetracyclododecene, tricyclodecene, tricycloundecene, pentacyclopentadecene, pentacyclohexadecene, 8-methyltetracyclododecene, 8-ethyltetracyclododecene, 5-acetylnorbornene, 5-acetyloxynorbornene, 5-methoxycarbonylnorbornene, 5-ethoxycarbonylnorbornene, 5-methyl-5-methoxycarbonylnorbornene, 5-cyanonorbornene, 8-methoxycarbonyltetracyclododecene, 8-methyl-8-tetracyclododecene, and 8-cyanotetracyclododecene; an alkenylalicyclic compound such as vinylcyclohexane; an alkenylaromatic hydrocarbon such as styrene, an alkenylbenzene (for example, 2-phenylpropylene, 2-phenylbutene and 3-phenylpropylene), an alkylstyrene (for example, p-methylstyrene, m-methylstyrene, o-methyl styrene, p-ethylstyrene, m-ethylstyrene, o-ethylstyrene, α-methylstyrene, 2,4-dimethylstyrene, 2,5-dimethylstyrene, 3,4-dimethylstyrene, 3,5-dimethylstyrene, 3-methyl-5-ethylstyrene, p-tert-butylstyrene and p-sec-butylstyrene), a bisalkenylbenzene (for example, divinylbenzene), and an alkenylnaphthalene (for example, 1-vinylnaphthalene); and following polar monomers (1) to (6):

(1) an α,β-unsaturated carboxylic acid such as acrylic acid, methacrylic acid, fumaric acid, maleic anhydride, itaconic acid, itaconic anhydride and bicyclo(2,2,1)-5-heptene-2,3-dicarboxylic acid;

(2) a salt of the above α,β-unsaturated carboxylic acid with a metal (for example, sodium, potassium, lithium, zinc, magnesium and calcium);

(3) an α,β-unsaturated carboxylic acid ester such as methyl acrylate, ethyl acrylate, n-propyl acrylate, isopropyl acrylate, t-butyl acrylate, 2-ethylhexyl acrylate, methyl methacrylate, ethyl methacrylate, n-propyl methacrylate, isopropyl methacrylate, n-butyl methacrylate and isobutyl methacrylate;

(4) an unsaturated dicarboxylic acid such as maleic acid and itaconic acid;

(5) a vinyl ester such as vinyl acetate, vinyl propionate, vinyl caproate, vinyl caprate, vinyl laurate, vinyl stearate and vinyl trifluoroacetate; and (6) an unsaturated carboxylic acid glycidyl ester such as glycidyl acrylate, glycidyl methacrylate and itaconic acid mono-glycidyl ester.

Examples of the addition polymer in the present invention are a copolymer of ethylene with an α-olefin having 3 to 20 carbon atoms such as an ethylene-propylene copolymer, an ethylene-1-butene copolymer, an ethylene-1-hexene copolymer, an ethylene-1-octene copolymer, and an ethylene-vinylcyclohexane copolymer; a copolymer of propylene with an α-olefin having 4 to 20 carbon atoms such as a propylene-1-butene copolymer, a propylene-1-hexene copolymer, and a propylene-vinylcyclohexane copolymer; a copolymer of ethylene, propylene and an α-olefin having 4 to 20 carbon atoms such as an ethylene-propylene-1-butene copolymer, an ethylene-propylene-1-hexene copolymer, and an ethylene-propylene-vinylcyclohexane copolymer; and a homopolymer of ethylene or an α-olefin having 3 to 20 carbon atoms such as an ethylene homopolymer, a propylene homopolymer, a 1-butene homopolymer, a 1-hexene homopolymer, and a vinylcyclohexane homopolymer.

EXAMPLE

The present invention is explained in more detail with reference to the following Examples, which do not limit the present invention.

Example 1

(1) Production of Contact Product

To a 100 mL flask were charged 6 mL of water and 4.6 g of zinc oxide, and then 12.0 mL of trifluoroacetic acid (compound represented by formula [1]) was added thereto by drops at room temperature, wherein a molar amount of an active hydrogen contained in trifluoroacetic acid used was 2.8 mol per one mol of a zinc atom contained in zinc oxide used. The resultant mixture was stirred for three hours at room temperature, and then the reaction mixture was filtered. Volatile matters contained in the separated solid were distilled away under reduced pressure. The resultant white solid was dried at 120° C. for four hours under reduced pressure, thereby obtaining 8.6 g of a contact product having the following NMR data:

$^{13}$C-NMR (D$_2$O): δ162.8 (t, JC-F=35.5 Hz), 81.1 (q, JC-F=291 Hz); and $^{19}$F-NMR (D$_2$O): δ−72.0 (s).

(2) Polymerization

A 400 mL autoclave equipped with a stirrer was vacuum-dried, and was purged with argon gas. To the autoclave were charged 190 mL of toluene (solvent) and 10 mL of 1-hexene (comonomer). The autoclave was heated up to 70° C., and then was charged with ethylene under regulating its pressure at 6 MPa. To the autoclave were charged 0.25 mmol of tri-isobutylaluminum (organoaluminum compound), 0.2 mL (containing 0.2 μmol of bis(n-butylcyclopentadienyl) zirconium dichloride) of a toluene solution (concentration: 1 μmol/mL) of bis(n-butylcyclopentadienyl)zirconium dichloride (transition metal compound), and 30 mg (containing 103 μmol of a zinc atom) of the above-obtained contact product (catalyst component for addition polymerization), in this order, to initiate polymerization. The polymerization was carried out at 70° C. for 30 minutes, thereby obtaining 1.2 g of an ethylene-1-hexene copolymer. Its polymerization activity was found to be $1.2 \times 10^7$ g-copolymer/mol-Zr/hour. The copolymer was found to have a short-chain branch number per 1,000 carbon atoms (referred to hereinafter as "SCB") of 1.4; melting temperature of 121.7° C.; weight average molecular weight (Mw) of 527,000; and molecular weight distribution (Mw/Mn, Mn: number average molecular weight) of 2.5. Results are shown in Table 1.

The above $^{13}$C-NMR (D$_2$O) and $^{19}$F-NMR (D$_2$O) were measured using an NMR apparatus, JNM-AL400, manufactured by JEOL LTD., at room temperature, wherein a hexafluorobenzene-sealed glass capillary (external standard) was put in an NMR sample tube.

The above melting temperature was measured using a differential scanning calorimeter, DIAMOND DSC, manufactured by Perkin Elmer, by a method comprising steps of:

(1) keeping about 10 mg of a sample at 150° C. for 5 minutes in a nitrogen atmosphere;

(2) cooling the sample down to 20° C. at a cooling rate of 5° C./minute, and keeping the sample for 2 minutes;

(3) heating the sample up to 150° C. at a heating rate of 5° C./minute, thereby obtaining an endothermic curve; and (4) considering peak temperature in the endothermic curve as melting temperature of the sample.

The above SCB corresponds to the number of 1-hexene units per 1,000 carbon atoms contained in the ethylene-1-hexene copolymer, and was measured by infrared spectroscopy using an infrared spectrometer, EQUINOX 55, manufactured by Bruker Corporation, based on characteristic absorptions (1,378 cm$^{-1}$ to 1,303 cm$^{-1}$) of a butyl group contained in the 1-hexene unit.

The above average molecular weight and molecular weight distribution were measured by gel permeation chromatography (GPC) under the following conditions, a calibration curve being prepared using standard polystyrene:

equipment: type 150C, manufactured by Millipore Waters Co.;

column: TSK-GEL GMH-HT, 7.5 mm (inner diameter)×600 mm (length)×2 columns;

measurement temperature: 140° C. or 152° C.;

solvent: ortho-dichlorobenzene; and measurement concentration: 5 mg/5 ml.

Example 2

(1) Production of Contact Product

To a 50 mL flask were charged 2 mL of water and 0.81 g of zinc oxide, and then 2.1 mL of pentafluoropropionic acid (compound represented by formula [1]) was added thereto by drops at room temperature, wherein a molar amount of an active hydrogen contained in pentafluoropropionic acid was 2.0 mol per one mol of a zinc atom contained in zinc oxide used. The resultant mixture was stirred for three hours at room temperature, and then the reaction mixture was filtered. Volatile matters contained in the separated solid were distilled away under reduced pressure. The resultant white solid was dried at 120° C. for four hours under reduced pressure, thereby obtaining 3.0 g of a contact product (catalyst component for addition polymerization) having the following NMR data:

$^{13}$C-NMR (D$_2$O): δ163.2 (t, JC-F=24.8 Hz), 118.1 (qt, J1C-F=285 Hz, J2C-F=35.5 Hz), 106.7 (tq, J1C-F=263 Hz, J2C-F=37.2 Hz); and $^{19}$F-NMR (D$_2$O): δ−79.6 (s), −117.3 (s).

(2) Polymerization

Example 1 was repeated except that 30 mg (containing 103 μmol of a zinc atom) of the catalyst component for addition polymerization was changed to 35 mg (containing 89 μmol of a zinc atom) of the above-obtained catalyst component for addition polymerization, thereby obtaining 0.36 g of an ethylene-1-hexene copolymer. Its polymerization activity was found to be 3.6×10$^6$ g-copolymer/mol-Zr/hour. The copolymer was found to have an SCB of 2.0; melting temperature of 125.3° C.; weight average molecular weight (Mw) of 430,000; and molecular weight distribution (Mw/Mn) of 4.2. Results are shown in Table 1.

Example 3

(1) Production of Contact Product

Example 2 was repeated except that (i) 2 mL of water was changed to 3 mL thereof, and (ii) 2.1 mL of pentafluoropropionic acid was changed to 2.6 mL of heptafluorobutyric acid (compound represented by formula [1]), wherein a molar amount of an active hydrogen contained in heptafluorobutyric acid used was 2.0 mol per one mol of a zinc atom contained in zinc oxide used, thereby obtaining 3.5 g of a white contact product (catalyst component for addition polymerization) having the following NMR data:

$^{13}$C-NMR (D$_2$O): δ163.0 (t, JC-F=24.8 Hz), 117.2 (m), 108.3 (m), 108.2 (m); and $^{19}$F-NMR (D$_2$O): δ−77.5 (s), −115.1 (s), −124.1 (s).

(2) Polymerization

Example 1 was repeated except that (i) 0.2 mL of the toluene solution was changed to 0.4 mL (containing 0.4 mmol of bis(n-butylcyclopentadienyl)zirconium dichloride) thereof, and (ii) 30 mg (containing 103 mmol of a zinc atom) of the catalyst component for addition polymerization was changed to 52 mg (containing 106 μmol of a zinc atom) of the above-obtained catalyst component for addition polymerization, thereby obtaining 0.57 g of an ethylene-1-hexene copolymer. Its polymerization activity was found to be 2.9×10$^6$ g-copolymer/mol-Zr/hour. The copolymer was found to have an SCB of 1.8; melting temperature of 121.6° C.; weight average molecular weight (Mw) of 481,000; and molecular weight distribution (Mw/Mn) of 3.7. Results are shown in Table 1.

Example 4

(1) Production of Contact Product

Example 2 was repeated except that (i) 2 mL of water was changed to 3 mL thereof, (ii) 0.81 g of zinc oxide was changed to 0.44 g thereof, and (iii) 2.1 mL of pentafluoropropionic acid was changed to 2.0 g of 3,3,3-trifluoro-2-trifluoromethylpropionic acid (compound represented by formula [1]) added little by little, wherein a molar amount of an active hydrogen contained in 3,3,3-trifluoro-2-trifluoromethylpropionic acid used was 1.8 mol per one mol of a zinc atom contained in zinc oxide used, thereby obtaining 1.7 g of a white contact product (catalyst component for addition polymerization) having the following NMR data:

$^1$H-NMR (D$_2$O): δ4.0 (m);

$^{13}$C-NMR (D$_2$O): δ165.1 (s), 121.8 (q, JC-F=275.3 Hz), 55.5 (m, JC-F=28.1 Hz); and $^{19}$F-NMR (D$_2$O): δ−114.2 (s).

(2) Polymerization

Example 1 was repeated except that 30 mg (containing 103 μmol of a zinc atom) of the catalyst component for addition polymerization was changed to 49 mg (containing 108 μmol of a zinc atom) of the above-obtained catalyst component for addition polymerization, thereby obtaining 3.0 g of an ethylene-1-hexene copolymer. Its polymerization activity was found to be 3.0×10$^7$ g-copolymer/mol-Zr/hour. The copolymer was found to have an SCB of 1.4; melting temperature of 121.2° C.; weight average molecular weight (Mw) of 473,000; and molecular weight distribution (Mw/Mn) of 2.5. Results are shown in Table 1.

The above 1H-NMR (D$_2$O) was measured with an NMR apparatus, JNM-AL400, manufactured by JEOL LTD., using D$_2$O as a solvent, at room temperature based on a chemical shift value of a hydrogen atom of DHO.

Example 5

(1) Production of Contact Product

Example 2 was repeated except that (i) 2 mL of water was changed to 3 mL thereof, (ii) 0.81 g of zinc oxide was changed to 0.44 g thereof, and (iii) 2.1 mL of pentafluoropropionic acid was changed to 0.95 g of tetrafluorosuccinic acid (compound represented by formula [1]) added little by little, wherein a molar amount of an active hydrogen contained in tetrafluorosuccinic acid used was 1.8 mol per one mol of a zinc atom contained in zinc oxide used, thereby obtaining 0.8 g of a white contact product (catalyst component for addition polymerization) having the following NMR data:

13C-NMR (D$_2$O): δ165.2 (t, JC-F=26.4 HZ), 109.8 (tt, J1C-F=260 Hz, J2C-F=33.8 Hz); and $^{19}$F-NMR (D$_2$O): δ−114.2 (s).

(2) Polymerization

Example 1 was repeated except that 30 mg (containing 103 μmol of a zinc atom) of the catalyst component for addition polymerization was changed to 26 mg (containing 103 μmol of a zinc atom) of the above-obtained catalyst component for addition polymerization, thereby obtaining 6.7 g of an ethylene-1-hexene copolymer. Its polymerization activity was found to be 6.7×10$^7$ g-copolymer/mol-Zr/hour. The copolymer was found to have an SCB of 2.9; melting temperature of 117.3° C.; weight average molecular weight (Mw) of 466,000; and molecular weight distribution (Mw/Mn) of 2.8. Results are shown in Table 1.

Example 6

(1) Production of Contact Product

Example 2 was repeated except that (i) 2 mL of water was changed to 3 mL thereof, (ii) 0.81 g of zinc oxide was changed to 1.8 g thereof, and (iii) 2.1 mL of pentafluoropropionic acid was changed to 4.8 g of hexafluoroglutaric acid (compound represented by formula [1]) added little by little, wherein a molar amount of an active hydrogen contained in hexafluoroglutaric acid used was 1.8 mol per one mol of a zinc atom contained in zinc oxide used, thereby obtaining 4.9 g of a white contact product (catalyst component for addition polymerization) having the following NMR data:

$^{13}$C-NMR (D$_2$O): δ164.0 (t, JC-F=25.7 HZ), 110.6 (m), 109.2 (m); and $^{19}$F-NMR (D$_2$O): δ−113.7 (s), −120.5 (s).

(2) Polymerization

Example 1 was repeated except that (i) 0.2 mL of the toluene solution was changed to 0.4 mL (containing 0.4 μmol of bis(n-butylcyclopentadienyl)zirconium dichloride) thereof, and (ii) 30 mg (containing 103 μmol of a zinc atom) of the catalyst component for addition polymerization was changed to 25 mg (containing 82 μmol of a zinc atom) of the above-obtained catalyst component for addition polymerization, thereby obtaining 3.0 g of an ethylene-1-hexene copolymer. Its polymerization activity was found to be 1.5×10$^7$ g-copolymer/mol-Zr/hour. The copolymer was found to have an SCB of 1.7; melting temperature of 120.8° C.; weight average molecular weight (Mw) of 496,000; and molecular weight distribution (Mw/Mn) of 2.5. Results are shown in Table 1.

Example 7

(1) Production of Contact Product

Example 2 was repeated except that (i) 2 mL of water was changed to 3 mL thereof, (ii) 0.81 g of zinc oxide was changed to 0.44 g thereof, and (iii) 2.1 mL of pentafluoropropionic acid was changed to 1.45 g of octafluoroadipic acid (compound represented by formula [1]) added little by little, wherein a molar amount of an active hydrogen contained in octafluoroadipic acid used was 1.8 mol per one mol of a zinc atom contained in zinc oxide used, thereby obtaining 2.6 g of a white contact product (catalyst component for addition polymerization) having the following NMR data:

$^{13}$C-NMR (D$_2$O): δ163.5 (t, JC-F=25.1 HZ), 115-105 (m); and $^{19}$F-NMR (D$_2$O): δ−114.0 (s), −119.7 (s).

(2) Polymerization

Example 1 was repeated except that 30 mg (containing 103 μmol of a zinc atom) of the catalyst component for addition polymerization was changed to 35 mg (containing 99 μmol of a zinc atom) of the above-obtained catalyst component for addition polymerization, thereby obtaining 4.3 g of an ethylene-1-hexene copolymer. Its polymerization activity was found to be 4.3×10$^7$ g-copolymer/mol-Zr/hour. The copolymer was found to have an SCB of 3.3; melting temperature of 117.4° C.; weight average molecular weight (Mw) of 466,000; and molecular weight distribution (Mw/Mn) of 3.5. Results are shown in Table 1.

Example 8

(1) Production of Contact Product

Example 2 was repeated except that (i) 2 mL of water was changed to 3 mL thereof, (ii) 0.81 g of zinc oxide was changed to 0.44 g thereof, and (iii) 2.1 mL of pentafluoropropionic acid was changed to 2.0 g of dodecafluorosuberic acid (compound represented by formula [1]) added little by little, wherein a molar amount of an active hydrogen contained in dodecafluorosuberic acid used was 1.8 mol per one mol of a zinc atom contained in zinc oxide used, thereby obtaining 1.7 g of a white contact product (catalyst component for addition polymerization) having the following NMR data:

$^{13}$C-NMR (D$_2$O): δ163.2 (t, JC-F=25.6 HZ), 115-105 (m); and $^{19}$F-NMR (D$_2$O): δ−113.9 (s), −118.3 (s), −120.0 (s).

(2) Polymerization

Example 1 was repeated except that 30 mg (containing 103 μmol of a zinc atom) of the catalyst component for addition polymerization was changed to 44 mg (containing 97 μmol of a zinc atom) of the above-obtained catalyst component for addition polymerization, thereby obtaining 5.0 g of an ethylene-1-hexene copolymer. Its polymerization activity was found to be 5.0×10$^7$ g-copolymer/mol-Zr/hour. The copolymer was found to have an SCB of 1.6; melting temperature of 118.7° C.; weight average molecular weight (Mw) of 496,000; and molecular weight distribution (Mw/Mn) of 2.8. Results are shown in Table 1.

Example 9

(1) Production of Contact Product

Example 2 was repeated except that (i) 2 mL of water was changed to 3 mL thereof, (ii) 0.81 g of zinc oxide was changed to 0.88 g thereof, and (iii) 2.1 mL of pentafluoropropionic acid was changed to 4.9 g of hexadecafluorosebacic acid (compound represented by formula [1]) added little by little, wherein a molar amount of an active hydrogen contained in hexadecafluorosebacic acid used was 1.8 mol per one mol of a zinc atom contained in zinc oxide used, thereby obtaining 4.3 g of a white contact product (catalyst component for addition polymerization) having the following NMR data:

$^{13}$C-NMR (D$_2$O): δ164.0 (t, JC-F=24.8 HZ), 115-105 (m); and $^{19}$F-NMR (D$_2$O): δ−113.9 (s), −118.2 (s), −119.6 (s).

(2) Polymerization

Example 1 was repeated except that 30 mg (containing 103 μmol of a zinc atom) of the catalyst component for addition polymerization was changed to 57 mg (containing 103 μmol of a zinc atom) of the above-obtained catalyst component for addition polymerization, thereby obtaining 2.0 g of an ethylene-1-hexene copolymer. Its polymerization activity was found to be 2.0×10$^7$ g-copolymer/mol-Zr/hour. The copolymer was found to have an SCB of 0.4; melting temperature of 120.3° C.; weight average molecular weight (Mw) of 552,000; and molecular weight distribution (Mw/Mn) of 2.6. Results are shown in Table 1.

Example 10

(1) Production of Contact Product

Example 2 was repeated except that (i) 2 mL of water was changed to 3 mL thereof, (ii) 0.81 g of zinc oxide was changed to 0.44 g thereof, and (iii) 2.1 mL of pentafluoropropionic acid was changed to 0.88 mL of trifluoromethanesulfonic acid (compound represented by formula [2]), wherein a molar amount of an active hydrogen contained in trifluoromethanesulfonic acid used was 1.8 mol per one mol of a zinc atom contained in zinc oxide used, thereby obtaining 1.3 g of a white contact product (catalyst component for addition polymerization) having the following NMR data:
$^{13}$C-NMR (D$_2$O): δ119.4 (q, JC-F=316.6 HZ); and
$^{19}$F-NMR (D$_2$O): δ–75.1 (s).

(2) Polymerization

Example 1 was repeated except that 30 mg (containing 103 μmol of a zinc atom) of the catalyst component for addition polymerization was changed to 39 mg (containing 107 μmol of a zinc atom) of the above-obtained catalyst component for addition polymerization, thereby obtaining 5.8 g of an ethylene-1-hexene copolymer. Its polymerization activity was found to be 5.8×10$^7$ g-copolymer/mol-Zr/hour. The copolymer was found to have an SCB of 2.6; melting temperature of 118.7° C.; weight average molecular weight (Mw) of 418,000; and molecular weight distribution (Mw/Mn) of 2.6. Results are shown in Table 1

Comparative Example 1

(1) Synthesis of bis(pentafluorophenoxy)zinc disclosed in JP 2001-181327A

A four-necked 200 mL flask was dried under reduced pressure, and then was purged with argon. To the flask were charged 50 mL of hexane and 10 mL (containing 10 mmol of diethylzinc) of a hexane solution (concentration: 1.00 mol/L) of diethylzinc. The resultant mixture was cooled down to −78° C., and 20 mL (containing 20 mmol of pentafluorophenol) of a hexane solution (concentration: 1.0 mol/L) of pentafluorophenol was added gradually to the flask by drops. The mixture in the flask became white slurry along with the reaction procedure. After completion of the addition of pentafluorophenol, the mixture was heated gradually up to room temperature, and was stirred at room temperature for four hours. The obtained reaction mixture was filtered with a glass filter, thereby separating a white solid. The white solid was dried under reduced pressure, thereby obtaining 3.41 g (7.90 mmol, yield 79%) of bis(pentafluorophenoxy)zinc having the following NMR data:
$^{13}$C-NMR (THF-d8): δ141.4 (m, JC-F=233 HZ), 141.8 (m), 139.0 (m, JC-F=249 Hz), 131.7 (m, JC-F=236 Hz).

(2) Polymerization

Example 1 was repeated except that 30 mg (containing 103 μmol of a zinc atom) of the catalyst component for addition polymerization was changed to 54 mg (containing 125 μmol of a zinc atom) of the above-obtained bis(pentafluorophenoxy)zinc, thereby obtaining 3.0 g of an ethylene-1-hexene copolymer. Its polymerization activity was found to be 3.0×10$^7$ g-copolymer/mol-Zr/hour. The copolymer was found to have an SCB of 1.1; melting temperature of 120.9° C.; weight average molecular weight (Mw) of 336,000; and molecular weight distribution (Mw/Mn) of 2.6. Results are shown in Table 1.

The above $^{13}$C-NMR (THF-d8) was measured similarly to the above $^{13}$C-NMR (D$_2$O) measurement, provided that a chemical shift value of a carbon atom of THF-d8 was used as the base.

Comparative Example 2

(1) Production of Contact Product

To a two-necked 200 mL flask purged with nitrogen gas were charged 50 mL of toluene and 10 mL (containing 20 mmol of diethylzinc) of a hexane solution (concentration: 2.02 mmol/mL) of diethylzinc. To the flask dipped in a water bath were added separately by drops, 2.6 mL (20 mmol) of heptafluorobutyric acid (compound represented by formula [1]) and 180 μL (10 mmol) of water. After completion of the drop-wise addition, the mixture was heated up to 40° C., and was stirred for one our. The obtained reaction mixture was naturally-cooled down to room temperature, and was subjected to distillation under reduced pressure to distil away volatile matters. The resultant material was dried at 40° C. for four hours under reduced pressure, thereby obtaining 4.0 g of a white solid having the following NMR data:
$^{13}$C-NMR (THF-d8): δ5164.7 (m), 130-105 (m); and
$^{19}$F-NMR (THF-d8): δ–78.1 (s), –114.9 (m), –124.0 (m).

(2) Polymerization

Example 1 was repeated except that (i) 30 mg (containing 103 μmol of a zinc atom) of the catalyst component for addition polymerization was changed to 55 mg of the above-obtained white solid, and (ii) 0.2 mL of a toluene solution of bis(n-butylcyclopentadienyl)zirconium dichloride was changed to 0.2 mL (containing 0.2 μmol of ethylenebis(indenyl)zirconium dichloride) of a toluene solution (concentration: 1 μmol/mL) of ethylenebis(indenyl)zirconium dichloride, thereby obtaining 4.2 g of an ethylene-1-hexene copolymer. Its polymerization activity was found to be 4.2×10$^7$ g-copolymer/mol-Zr/hour. The copolymer was found to have an SCB of 10.3; melting temperature of 112.4° C.; weight average molecular weight (Mw) of 66,000; and molecular weight distribution (Mw/Mn) of 1.9. Results are shown in Table 1.

Example 11

Polymerization of Ethylene

A 400 mL autoclave equipped with a stirrer was vacuum-dried, and was purged with argon gas. The autoclave was charged with 200 mL of toluene (solvent), and was heated up to 40° C. Ethylene was charged to the autoclave under regulating its pressure at 6 MPa. To the autoclave were charged 0.25 mmol of triisobutylaluminum, 29 mg (containing 100 μmol of a zinc atom) of the catalyst component for addition polymerization obtained in Example 1, and 4.0 mL (containing 4.0 μmol of diacetylbis(2,6-diisopropylphenylimine) nickel dibromide) of a toluene slurry (concentration: 1 μmol/mL) of diacetylbis(2,6-diisopropylphenylimine)nickel dibromide (transition metal compound), in this order, to initiate polymerization. The polymerization was carried out at 40° C. for 30 minutes, thereby obtaining 3.4 g of an ethylene polymer. Its polymerization activity was found to be 1.7×10$^6$ g-polymer/mol-Zr/hour. The polymer was found to have an SCB of 90.2; melting temperature of 45.8° C.; weight average molecular weight (Mw) of 428,000; and molecular weight distribution (Mw/Mn) of 2.5. Results are shown in Table 2.

Examples 12 to 20

Example 11 was repeated except that (i) 29 mg of the catalyst component for addition polymerization obtained in Example 1, and (ii) 4.0 mL of the toluene slurry of diacetylbis(2,6-diisopropylphenylimine)nickel dibromide were changed respectively to those set forth in Table 2, thereby obtaining an ethylene polymer. Results are shown in Table 2.

TABLE 1

|  | Example | | | | | |
| --- | --- | --- | --- | --- | --- | --- |
|  | 1 | 2 | 3 | 4 | 5 | 6 |
| Production of catalyst component | | | | | | |
| Zinc oxide (g) | 4.6 | 0.81 | 0.81 | 0.44 | 0.44 | 1.8 |
| Compound represented by formula [1] or [2] | | | | | | |
| Trifluoroacetic acid (mL) | 12.0 | | | | | |
| Petafluoropropionic acid (mL) | | 2.1 | | | | |
| Heptafluorobutyric acid (mL) | | | 2.6 | | | |
| 3,3,3-Trifluoro-2-trifluoromethyl propionic acid (g) | | | | 2.0 | | |
| Tetrafluorosuccinic acid (g) | | | | | 0.95 | |
| Hexafluoroglutaric acid (g) | | | | | | 4.8 |
| Water (solvent, mL) | 6 | 2 | 3 | 3 | 3 | 3 |
| Molar ratio of H/Zn (Note 1) | 2.8 | 2.0 | 2.0 | 1.8 | 1.8 | 1.8 |
| Polymerization of ethylene with 1-hexene | | | | | | |
| Amount of Zn atom contained in catalyst component used (μmol) | 103 | 89 | 106 | 108 | 103 | 82 |
| Polymerization activity (g-polymer/mol-Zr/h) | $1.2 \times 10^7$ | $3.6 \times 10^6$ | $2.9 \times 10^6$ | $3.0 \times 10^7$ | $6.7 \times 10^7$ | $1.5 \times 10^7$ |
| SCB | 1.4 | 2.0 | 1.8 | 1.4 | 2.9 | 1.7 |
| Melting temperature (° C.) | 121.7 | 125.3 | 121.6 | 121.2 | 117.3 | 120.8 |
| Mw (×10³) | 527 | 430 | 481 | 473 | 466 | 496 |
| Mw/Mn | 2.5 | 4.2 | 3.7 | 2.5 | 2.8 | 2.5 |

|  | Example | | | | Comp. Example | |
| --- | --- | --- | --- | --- | --- | --- |
|  | 7 | 8 | 9 | 10 | 1 | 2 |
| Production of catalyst component | | | | | (Note 2) | |
| Zinc oxide (g) | 0.44 | 0.44 | 0.88 | 0.44 | | |
| Compound represented by formula [1] or [2] | | | | | | |
| Octafluoroadipic acid (g) | 1.45 | | | | | |
| Dodecafluorosuberic acid (g) | | 2.0 | | | | |
| Hexadecafluorosebacic acid (g) | | | 4.9 | | | |
| Trifluoromethanesulfonic acid (mL) | | | | 0.88 | | |
| Water (solvent, mL) | 3 | 3 | 3 | 3 | | |
| Molar ratio of H/Zn (Note 1) | 1.8 | 1.8 | 1.8 | 1.8 | | |
| Polymerization of ethylene with 1-hexene | | | | | | |
| Amount of Zn atom contained in catalyst component used (μmol) | 99 | 97 | 103 | 107 | 125 | — |
| Polymerization activity (g-polymer/mol-Zr/h) | $4.3 \times 10^7$ | $5.0 \times 10^7$ | $2.0 \times 10^7$ | $5.8 \times 10^7$ | $5.0 \times 10^7$ | $4.2 \times 10^7$ |
| SCB | 3.3 | 1.6 | 0.4 | 2.6 | 1.1 | 10.3 |
| Melting temperature (° C.) | 117.4 | 118.7 | 120.3 | 118.7 | 120.9 | 112.4 |
| Mw (×10³) | 466 | 496 | 552 | 418 | 336 | 66 |
| Mw/Mn | 3.5 | 2.8 | 2.6 | 2.6 | 2.6 | 1.9 |

(Note 1):
"H/Zn" means a molar amount of an active hydrogen contained in a compound represented by formula [1] or [2] used, per one mol of a zinc atom contained in zinc oxide used.

(Note 2):
As a catalyst component, Comparative Example 1 used 54 mg of bis(pentafluorophenoxy)zinc, and Comparative Example 2 used 55 mg of the white solid obtained by reacting diethylzinc with heptafluorobutyric acid.

TABLE 2

|  | Example | | | | |
| --- | --- | --- | --- | --- | --- |
|  | 11 | 12 | 13 | 14 | 15 |
| Example number in which catalyst component used in Examples 11-15 was produced | 1 | 2 | 3 | 4 | 5 |
| Polymerization of ethylene | | | | | |
| Amount of Zn atom contained in catalyst component used (μmol) | 100 | 91 | 105 | 109 | 110 |
| Amount of diacetylbis(2,6-diisopropylphenylimine) nickel dibromide (μmol) | 4.0 | 4.0 | 4.0 | 1.0 | 1.0 |

TABLE 2-continued

| | | | | | |
|---|---|---|---|---|---|
| Polymerization activity (g-polymer/mol-Zr/h) | $1.7 \times 10^6$ | $1.7 \times 10^6$ | $2.4 \times 10^6$ | $1.1 \times 10^6$ | $2.6 \times 10^6$ |
| SCB | 90.2 | 91.0 | 96.9 | 93.3 | 90.0 |
| Melting temperature (° C.) | 45.8 | 45.4 | 41.7 | 48.3 | 45.0 |
| Mw (×10³) | 428 | 384 | 412 | 398 | 432 |
| Mw/Mn | 2.5 | 2.7 | 2.5 | 2.6 | 2.6 |

| | Example | | | | |
|---|---|---|---|---|---|
| | 16 | 17 | 18 | 19 | 20 |
| Example number in which catalyst component used in Examples 16-20 was produced | 6 | 7 | 8 | 9 | 10 |
| Polymerization of ethylene | | | | | |
| Amount of Zn atom contained in catalyst component used (μmol) | 102 | 99 | 103 | 100 | 119 |
| Amount of diacetylbis(2,6-diisopropylphenylimine) nickel dibromide (μmol) | 4.0 | 1.0 | 1.0 | 1.0 | 1.0 |
| Polymerization activity (g-polymer/mol-Zr/h) | $2.3 \times 10^6$ | $2.2 \times 10^6$ | $2.1 \times 10^6$ | $2.4 \times 10^6$ | $2.1 \times 10^6$ |
| SCB | 102.9 | 89.6 | 90.3 | 97.7 | 93.0 |
| Melting temperature (° C.) | 37.5 | 46.5 | 46.5 | 43.2 | 46.5 |
| Mw (×10³) | 388 | 520 | 443 | 457 | 527 |
| Mw/Mn | 2.4 | 2.6 | 2.4 | 2.4 | 2.8 |

The invention claimed is:

1. A process for producing a contact product, comprising contacting a metal oxide with a compound represented by following formula [1] or [2]:

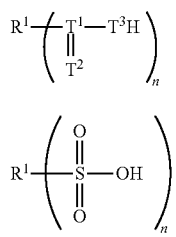

wherein $R^1$ is a monovalent, divalent, trivalent or tetravalent halogenated hydrocarbyl group having 1 to 20 carbon atoms; $T^1$ is a carbon atom or a sulfur atom; $T^2$ is an oxygen atom or a sulfur atom; $T^3$ is a group 16 atom of the periodic table; and n is an integer of 1 to 4, wherein the contacting the metal oxide with the compound represented by formula [1] or [2] is carried out in the presence of water.

2. The process according to claim 1, wherein the metal oxide is a metal oxide of an element selected from groups 1, 2 and 12 to 18 of the periodic table.

3. The process according to claim 1, wherein the metal oxide is a metal oxide of an element of group 12 of the periodic table.

4. The process according to claim 1, wherein the metal oxide is zinc oxide.

5. The process according to claim 1, wherein $T^1$ is a carbon atom.

6. The process according to claim 1, wherein $T^2$ is an oxygen atom.

7. The process according to claim 1, wherein $T^3$ is an oxygen atom.

8. The process according to claim 1, wherein $R^1$ is a fluorinated hydrocarbyl group having 1 to 20 carbon atoms.

9. The process according to claim 1, wherein $R^1$ is a fluorinated hydrocarbyl group having 2 to 10 carbon atoms.

10. The process according to claim 1, wherein the contact product is a catalyst component for addition polymerization.

11. A process for producing an addition polymerization catalyst, comprising contacting with one another a catalyst component for addition polymerization produced by the process of claim 10, a transition metal compound of groups 3 to 11 of the periodic table, and an optional organoaluminum compound.

12. A process for producing an addition polymer, comprising polymerizing an addition-polymerizable monomer in the presence of an addition polymerization catalyst, produced by the process of claim 11.

* * * * *